US012788611B2

(12) United States Patent
Xu et al.

(10) Patent No.: US 12,788,611 B2
(45) Date of Patent: Nov. 10, 2026

(54) FLUID COLLECTION WITH MULTIPORT VALVE ASSEMBLY

(71) Applicant: PureWick Corporation, El Cajon, CA (US)

(72) Inventors: Qihua Xu, Cary, NC (US); Hannah Rose Kriscovich, Marietta, GA (US); Jill W. Jones, Avondale Estates, GA (US); Juan Alejandro Saavedra Cisneros, Dacula, GA (US); Dennis Joseph, Milton, GA (US)

(73) Assignee: PUREWICK CORPORATION, Covington, GA (US)

( * ) Notice: Subject to any disclaimer, the term of this patent is extended or adjusted under 35 U.S.C. 154(b) by 752 days.

(21) Appl. No.: 17/929,887

(22) Filed: Sep. 6, 2022

(65) Prior Publication Data

US 2023/0073708 A1 Mar. 9, 2023

Related U.S. Application Data

(60) Provisional application No. 63/241,328, filed on Sep. 7, 2021.

(51) Int. Cl.
*A61F 5/44* (2006.01)
*A61F 5/455* (2006.01)

(52) U.S. Cl.
CPC .......... *A61F 5/4404* (2013.01); *A61F 5/4556* (2013.01)

(58) Field of Classification Search
CPC ............................ A61F 5/4404; A61F 5/4556
See application file for complete search history.

(56) References Cited

U.S. PATENT DOCUMENTS

| | | | |
|---|---|---|---|
| 670,602 | A | 3/1901 | Baker |
| 737,443 | A | 8/1903 | Mooers |
| 976,883 | A | 11/1910 | Keagy et al. |
| 1,015,905 | A | 1/1912 | Northrop |
| 1,032,841 | A | 7/1912 | Koenig |
| 1,178,644 | A | 4/1916 | Johnson |
| 1,229,423 | A | 6/1917 | Eckenrode |
| 1,387,726 | A | 8/1921 | Karge |
| 1,742,080 | A | 12/1929 | Jones |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Sandhausen et al. (withdrawn)

(Continued)

*Primary Examiner* — Kai H Weng
*Assistant Examiner* — Katherine-Ph Minh Pham
(74) *Attorney, Agent, or Firm* — Ballard Spahr LLP

(57) ABSTRACT

Embodiments of the invention relate to devices, systems, and methods for collecting fluid from a wearer. The fluid collection device includes a fluid impermeable barrier defining an interior chamber therein, a permeable body in the interior region, a conduit disposed within the interior chamber, and a multiport valve assembly. The multiport valve assembly allows a user to select a port at a longitudinal point in the interior chamber through which the collected valve can be removed.

22 Claims, 11 Drawing Sheets

(56) References Cited

U.S. PATENT DOCUMENTS

| | | | |
|---|---|---|---|
| 1,979,899 | A | 11/1934 | Obrien et al. |
| 2,241,010 | A | 5/1941 | Chipley |
| 2,262,772 | A | 11/1941 | Peder |
| 2,326,881 | A | 8/1943 | Packer |
| 2,379,346 | A | 6/1945 | Farrell |
| 2,485,555 | A | 10/1949 | Bester |
| 2,571,357 | A | 10/1951 | Charles |
| 2,613,670 | A | 10/1952 | Edward |
| 2,616,426 | A | 11/1952 | Adele |
| 2,644,234 | A | 7/1953 | Earl |
| 2,648,335 | A | 8/1953 | Chambers |
| 2,789,560 | A | 4/1957 | Weimer |
| 2,859,786 | A | 11/1958 | Tupper |
| 2,944,551 | A | 7/1960 | Carl |
| 2,968,046 | A | 1/1961 | Duke |
| 2,971,512 | A | 2/1961 | Reinhardt |
| 3,032,038 | A | 5/1962 | Swinn |
| 3,077,883 | A | 2/1963 | Hill |
| 3,087,938 | A | 4/1963 | Hans et al. |
| 3,114,916 | A | 12/1963 | Hadley |
| 3,169,528 | A | 2/1965 | Knox et al. |
| 3,171,506 | A | 3/1965 | Therkel |
| 3,175,719 | A | 3/1965 | Herndon |
| 3,194,238 | A | 7/1965 | Breece |
| 3,198,994 | A | 8/1965 | Hildebrandt et al. |
| 3,221,742 | A | 12/1965 | Egon |
| 3,312,221 | A | 4/1967 | Overment |
| 3,312,981 | A | 4/1967 | McGuire et al. |
| 3,340,876 | A | 9/1967 | Hill |
| 3,349,768 | A | 10/1967 | Keane |
| 3,356,091 | A | 12/1967 | Patterson |
| 3,362,590 | A | 1/1968 | Gene |
| 3,366,116 | A | 1/1968 | Huck |
| 3,368,564 | A | 2/1968 | Selix |
| 3,369,940 | A | 2/1968 | Slautterback |
| 3,398,848 | A | 8/1968 | Donovan |
| 3,400,717 | A | 9/1968 | Bruce et al. |
| 3,406,688 | A | 10/1968 | Bruce |
| 3,411,504 | A | 11/1968 | Glassman |
| 3,424,163 | A | 1/1969 | Gravdahl |
| 3,425,471 | A | 2/1969 | Yates |
| 3,434,565 | A | 3/1969 | Fischer |
| 3,447,536 | A | 6/1969 | Snyder |
| 3,511,241 | A | 5/1970 | Lee |
| 3,512,185 | A | 5/1970 | Ellis |
| 3,520,300 | A | 7/1970 | Flower |
| 3,528,423 | A | 9/1970 | Lee |
| 3,608,552 | A | 9/1971 | Broerman |
| 3,613,123 | A | 10/1971 | Langstrom |
| 3,648,700 | A | 3/1972 | Warner |
| 3,651,810 | A | 3/1972 | Ormerod |
| 3,661,155 | A | 5/1972 | Lindan |
| 3,683,918 | A | 8/1972 | Pizzella |
| 3,690,315 | A | 9/1972 | Chittenden et al. |
| 3,699,815 | A | 10/1972 | Holbrook |
| 3,720,554 | A | 3/1973 | Stumpf |
| 3,721,243 | A | 3/1973 | Greth et al. |
| 3,726,277 | A | 4/1973 | Hirschman |
| 3,727,788 | A | 4/1973 | Holbrook |
| 3,730,411 | A | 5/1973 | Brockmuller |
| 3,742,952 | A | 7/1973 | Magers et al. |
| 3,742,953 | A | 7/1973 | Lee |
| 3,757,355 | A | 9/1973 | Allen et al. |
| 3,788,324 | A | 1/1974 | Lim |
| 3,843,016 | A | 10/1974 | Bornhorst et al. |
| 3,863,638 | A | 2/1975 | Rogers et al. |
| 3,863,798 | A | 2/1975 | Kurihara et al. |
| 3,864,759 | A | 2/1975 | Horiuchi |
| 3,865,109 | A | 2/1975 | Elmore et al. |
| 3,881,486 | A | 5/1975 | Fenton |
| 3,881,489 | A | 5/1975 | Hartwell |
| 3,915,189 | A | 10/1975 | Holbrook et al. |
| 3,931,650 | A | 1/1976 | Miller |
| 3,931,819 | A | 1/1976 | Weedle |
| 3,964,786 | A | 6/1976 | Mashuda |
| 3,998,228 | A | 12/1976 | Poidomani |
| 3,999,550 | A | 12/1976 | Martin |
| 4,006,793 | A | 2/1977 | Robinson |
| 4,015,604 | A | 4/1977 | Csillag |
| 4,020,843 | A | 5/1977 | Kanall |
| 4,022,211 | A | 5/1977 | Timmons et al. |
| 4,022,213 | A | 5/1977 | Stein |
| 4,023,216 | A | 5/1977 | Li |
| 4,027,776 | A | 6/1977 | Douglas |
| 4,031,897 | A | 6/1977 | Graetz |
| 4,042,337 | A | 8/1977 | Griffith |
| 4,064,962 | A | 12/1977 | Hunt |
| 4,069,817 | A | 1/1978 | Fenole et al. |
| 4,084,589 | A | 4/1978 | Kulvi |
| 4,096,897 | A | 6/1978 | Cammarata |
| 4,116,197 | A | 9/1978 | Bermingham |
| 4,140,739 | A | 2/1979 | Cotten |
| 4,180,178 | A | 12/1979 | Turner |
| 4,187,953 | A | 2/1980 | Turner |
| 4,194,508 | A | 3/1980 | Anderson |
| 4,197,849 | A | 4/1980 | Bostick |
| 4,200,102 | A | 4/1980 | Duhamel et al. |
| 4,202,058 | A | 5/1980 | Anderson |
| 4,203,503 | A | 5/1980 | Bertotti et al. |
| 4,209,076 | A | 6/1980 | Bertotti et al. |
| D255,935 | S | 7/1980 | Cullis et al. |
| 4,223,677 | A | 9/1980 | Anderson |
| 4,233,025 | A | 11/1980 | Larson et al. |
| 4,233,978 | A | 11/1980 | Hickey |
| 4,246,901 | A | 1/1981 | Frosch et al. |
| 4,253,542 | A | 3/1981 | Ruspa et al. |
| 4,257,418 | A | 3/1981 | Hessner |
| 4,270,539 | A | 6/1981 | Frosch et al. |
| 4,280,498 | A | 7/1981 | Jensen |
| 4,281,655 | A | 8/1981 | Terauchi |
| 4,292,916 | A | 10/1981 | Bradley et al. |
| 4,330,239 | A | 5/1982 | Gannaway |
| 4,345,341 | A | 8/1982 | Saito |
| 4,349,029 | A | 9/1982 | Mott |
| 4,352,356 | A | 10/1982 | Tong |
| 4,356,012 | A | 10/1982 | Hofstetter |
| 4,360,933 | A | 11/1982 | Kimura et al. |
| 4,365,363 | A | 12/1982 | Windauer |
| 4,372,299 | A | 2/1983 | Fixel |
| 4,375,841 | A | 3/1983 | Vielbig |
| 4,387,726 | A | 6/1983 | Denard |
| 4,403,991 | A | 9/1983 | Hill |
| 4,421,511 | A | 12/1983 | Steer et al. |
| 4,425,130 | A | 1/1984 | Desmarais |
| 4,446,986 | A | 5/1984 | Bowen et al. |
| 4,453,938 | A | 6/1984 | Brendling |
| 4,457,314 | A | 7/1984 | Knowles |
| 4,457,758 | A | 7/1984 | Norton |
| 4,476,879 | A | 10/1984 | Jackson |
| 4,512,771 | A | 4/1985 | Norton |
| 4,526,688 | A | 7/1985 | Schmidt et al. |
| 4,528,703 | A | 7/1985 | Kraus |
| 4,533,354 | A | 8/1985 | Jensen et al. |
| 4,533,357 | A | 8/1985 | Hall |
| D280,438 | S | 9/1985 | Wendt |
| 4,551,141 | A | 11/1985 | Mcneil |
| 4,553,968 | A | 11/1985 | Komis |
| 4,568,341 | A | 2/1986 | Mitchell et al. |
| 4,581,026 | A | 4/1986 | Schneider |
| 4,583,983 | A | 4/1986 | Einhorn et al. |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,645,275 | A | 2/1987 | Pucci |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |

(56) References Cited

U.S. PATENT DOCUMENTS

| | | | |
|---|---|---|---|
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,759,753 | A | 7/1988 | Schneider et al. |
| 4,769,215 | A | 9/1988 | Ehrenkranz |
| 4,771,484 | A | 9/1988 | Mozell |
| 4,772,280 | A | 9/1988 | Rooyakkers |
| 4,775,458 | A | 10/1988 | Forester |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Schultz et al. |
| 4,846,909 | A | 7/1989 | Klug et al. |
| 4,857,064 | A | 8/1989 | Mendoza |
| 4,865,595 | A | 9/1989 | Heyden |
| 4,872,299 | A | 10/1989 | Troutner et al. |
| 4,875,898 | A | 10/1989 | Eakin |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-Ho |
| 4,895,140 | A | 1/1990 | Bellak |
| 4,903,254 | A | 2/1990 | Haas |
| 4,904,248 | A | 2/1990 | Vaillancourt |
| D306,759 | S | 3/1990 | D'Alo |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,030,229 | A | 7/1991 | Yang |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | McGuire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,134,994 | A | 8/1992 | Say |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | McGuire |
| 5,234,419 | A | 8/1993 | Bryant et al. |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,294,983 | A | 3/1994 | Ersoz et al. |
| 5,295,979 | A | 3/1994 | Delaurentis et al. |
| 5,295,983 | A | 3/1994 | Kubo |
| 5,300,052 | A | 4/1994 | Kubo |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,334,176 | A | 8/1994 | Buenger et al. |
| 5,340,840 | A | 8/1994 | Park et al. |
| D354,129 | S | 1/1995 | Salvadori |
| D354,560 | S | 1/1995 | Chase |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,455,091 | A | 10/1995 | Oreglia et al. |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,525,407 | A | 6/1996 | Yang |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| 5,641,277 | A | 6/1997 | Gondek |
| D380,543 | S | 7/1997 | Piontek et al. |
| 5,662,633 | A | 9/1997 | Doak et al. |
| 5,674,212 | A | 10/1997 | Osborn et al. |
| 5,678,564 | A | 10/1997 | Lawrence et al. |
| 5,678,654 | A | 10/1997 | Uzawa |
| 5,681,297 | A | 10/1997 | Hashimoto et al. |
| 5,687,429 | A | 11/1997 | Rahlff |
| 5,695,485 | A | 12/1997 | Duperret et al. |
| 5,695,487 | A | 12/1997 | Cohen et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,735,837 | A | 4/1998 | Ishikawa |
| 5,752,944 | A | 5/1998 | Dann et al. |
| 5,763,333 | A | 6/1998 | Suzuki et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,859,393 | A | 1/1999 | Cummins et al. |

(56) References Cited

U.S. PATENT DOCUMENTS

| | | | |
|---|---|---|---|
| 5,865,378 | A | 2/1999 | Hollinshead et al. |
| 5,873,869 | A | 2/1999 | Hammons et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| 5,895,349 | A | 4/1999 | Tihon |
| D409,303 | S | 5/1999 | Oepping |
| 5,911,222 | A | 6/1999 | Lawrence et al. |
| 5,956,782 | A | 9/1999 | Olguin |
| 5,957,904 | A | 9/1999 | Holland |
| 5,968,026 | A | 10/1999 | Osborn et al. |
| 5,972,505 | A | 10/1999 | Phillips et al. |
| 6,007,524 | A | 12/1999 | Schneider |
| 6,007,526 | A | 12/1999 | Passalaqua et al. |
| D421,307 | S | 2/2000 | Harmanoglu |
| 6,039,060 | A | 3/2000 | Rower |
| 6,050,983 | A | 4/2000 | Moore et al. |
| 6,059,762 | A | 5/2000 | Boyer et al. |
| 6,061,905 | A | 5/2000 | Logic |
| 6,063,064 | A | 5/2000 | Tuckey et al. |
| 6,083,602 | A | 7/2000 | Caldwell et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,417,750 | B1 | 7/2002 | Sohn |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,526,603 | B1 | 3/2003 | Murphy |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,848,719 | B2 | 2/2005 | Rowley |
| 6,849,065 | B2 | 2/2005 | Schmidt et al. |
| 6,857,137 | B2 | 2/2005 | Otto |
| 6,878,647 | B1 | 4/2005 | Rezai et al. |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,018,367 | B2 | 3/2006 | Nava |
| 7,066,411 | B2 | 6/2006 | Male et al. |
| 7,087,043 | B2 | 8/2006 | Dolan |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |

(56) References Cited

U.S. PATENT DOCUMENTS

| | | | |
|---|---|---|---|
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,981,087 | B2 | 7/2011 | Gesler, III |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,075,538 | B2 | 12/2011 | Vernon |
| 8,083,094 | B2 | 12/2011 | Caulfield et al. |
| 8,128,608 | B2 | 3/2012 | Thevenin |
| 8,156,941 | B1 | 4/2012 | Simms |
| 8,167,860 | B1 | 5/2012 | Siegel |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,430,855 | B2 | 4/2013 | Burgess et al. |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 | 8/2013 | Simpson et al. |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,062 | B2 | 10/2013 | Kay |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,586,583 | B2 | 11/2013 | Hamblin et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,702,667 | B1 | 4/2014 | Johnson |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,740,852 | B2 | 6/2014 | Aviles |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,839,792 | B2 | 9/2014 | Brunner |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,415,191 | B2 | 8/2016 | Aviles |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,737,433 | B2 | 8/2017 | Joh |
| 9,752,564 | B2 | 9/2017 | Arceno et al. |
| 9,788,992 | B2 | 10/2017 | Harvie |
| D804,907 | S | 12/2017 | Sandoval |
| D806,236 | S | 12/2017 | Lin |
| 9,868,564 | B2 | 1/2018 | Mcgirr et al. |
| D814,239 | S | 4/2018 | Arora |
| D817,484 | S | 5/2018 | Lafond |
| 9,968,908 | B2 | 5/2018 | Ladrech et al. |
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Mllarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |

(56) References Cited

U.S. PATENT DOCUMENTS

| | | | |
|---|---|---|---|
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,623 | B2 | 10/2020 | VanMiddendorp et al. |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,020,567 | B2 | 6/2021 | Rule et al. |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| D941,998 | S | 1/2022 | Tretheway et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,446,174 | B2 | 9/2022 | Newton |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,806,266 | B2 | 11/2023 | Sanchez et al. |
| 11,813,189 | B2 | 11/2023 | Hussey et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,877,948 | B2 | 1/2024 | Pinlac |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| 12,048,644 | B2 | 7/2024 | Davis |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,121,468 | B2 | 10/2024 | Sanchez et al. |
| 12,133,813 | B2 | 11/2024 | Ulreich et al. |
| 12,138,195 | B2 | 11/2024 | Alder et al. |
| D1,054,019 | S | 12/2024 | Miyawaki |
| 12,161,579 | B2 | 12/2024 | Sanchez et al. |
| D1,059,585 | S | 1/2025 | Miyawaki |
| D1,059,586 | S | 1/2025 | Miyawaki |
| 12,186,229 | B2 | 1/2025 | Davis et al. |
| 12,193,962 | B2 | 1/2025 | Newton et al. |
| 12,208,031 | B2 | 1/2025 | Knapp et al. |
| 12,233,003 | B2 | 2/2025 | Newton |
| D1,067,424 | S | 3/2025 | Naughton et al. |
| 12,245,966 | B2 | 3/2025 | Newton |
| 12,257,173 | B2 | 3/2025 | Newton et al. |
| 12,274,638 | B2 | 4/2025 | Spector |
| D1,074,995 | S | 5/2025 | Laffay et al. |
| 12,324,765 | B2 | 6/2025 | Sanchez et al. |
| 12,350,190 | B2 | 7/2025 | Hughett, Sr. et al. |
| 12,447,042 | B2 | 10/2025 | Martin et al. |
| 12,465,515 | B2 | 11/2025 | Brooks |
| D1,104,255 | S | 12/2025 | Hanna et al. |
| D1,107,222 | S | 12/2025 | Ecklund et al. |
| 12,594,182 | B2 | 4/2026 | Davis et al. |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0033200 | A1 | 3/2002 | Alex et al. |
| 2002/0042945 | A1 | 4/2002 | Sands |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0018309 | A1 | 1/2003 | Breznock |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0074724 | A1 | 4/2003 | Sands |
| 2003/0097100 | A1 | 5/2003 | Watson |
| 2003/0120178 | A1 | 6/2003 | Heki |
| 2003/0129178 | A1 | 7/2003 | Wegman et al. |
| 2003/0132352 | A1 | 7/2003 | Weaver |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0002687 | A1 | 1/2004 | Burns et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0098794 | A1 | 5/2004 | Ernest et al. |
| 2004/0102753 | A1 | 5/2004 | Butler |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0147895 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0181201 | A1 | 9/2004 | Mizutani et al. |
| 2004/0187200 | A1 | 9/2004 | Otto et al. |
| 2004/0191919 | A1 | 9/2004 | Unger et al. |
| 2004/0194792 | A1 | 10/2004 | Zhuang et al. |
| 2004/0200936 | A1 | 10/2004 | Opperthauser |
| 2004/0207530 | A1 | 10/2004 | Nielsen |
| 2004/0215133 | A1 | 10/2004 | Weber et al. |
| 2004/0236292 | A1 | 11/2004 | Tazoe et al. |
| 2004/0243075 | A1 | 12/2004 | Harvie |
| 2004/0254547 | A1 | 12/2004 | Okabe et al. |

(56) References Cited

U.S. PATENT DOCUMENTS

2005/0010182 A1 1/2005 Parks et al.
2005/0010197 A1 1/2005 Lau et al.
2005/0033248 A1 2/2005 Machida et al.
2005/0065471 A1 3/2005 Kuntz
2005/0070861 A1 3/2005 Okabe et al.
2005/0070862 A1 3/2005 Tazoe et al.
2005/0082300 A1 4/2005 Modrell et al.
2005/0097662 A1 5/2005 Leimkuhler et al.
2005/0101924 A1 5/2005 Elson et al.
2005/0119630 A1 6/2005 Harvie
2005/0131361 A1 6/2005 Miskie
2005/0137557 A1 6/2005 Swiecicki et al.
2005/0137560 A1 6/2005 Mizutani et al.
2005/0137561 A1 6/2005 Mizutani et al.
2005/0148984 A1 7/2005 Lindsay et al.
2005/0154360 A1 7/2005 Harvie
2005/0177070 A1 8/2005 Levinson et al.
2005/0197639 A1 9/2005 Mombrinie
2005/0197645 A1 9/2005 Karpowicz et al.
2005/0215969 A1 9/2005 Mizutani et al.
2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 LeBlanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0069359 A1 3/2006 Dipalma et al.
2006/0079852 A1 4/2006 Bubb et al.
2006/0079854 A1 4/2006 Kay et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0032765 A1 2/2007 Honda
2007/0038194 A1 2/2007 Wada et al.
2007/0055209 A1 3/2007 Patel et al.
2007/0073252 A1 3/2007 Forgrave
2007/0106177 A1 5/2007 Hama
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0091162 A1 4/2008 Maldonado et al.
2008/0114327 A1 5/2008 Barge
2008/0140033 A1 6/2008 Burgess et al.
2008/0167634 A1 7/2008 Kouta et al.
2008/0183157 A1 7/2008 Walters
2008/0200884 A1 8/2008 Perkins et al.
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0199857 A1 8/2009 Peake et al.
2009/0226541 A1 9/2009 Scholz et al.
2009/0234312 A1 9/2009 Otoole et al.
2009/0247968 A1 10/2009 Brooks et al.
2009/0251510 A1 10/2009 Noro et al.
2009/0254040 A1 10/2009 Bierman et al.
2009/0259206 A1 10/2009 Kai et al.
2009/0264840 A1 10/2009 Mrginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0022011 A1 1/2011 Edward
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1 4/2011 Forsell
2011/0137273 A1 6/2011 Muellejans et al.
2011/0145993 A1 6/2011 Rader et al.
2011/0152802 A1 6/2011 Dicamillo et al.
2011/0152842 A1 6/2011 Graffam et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.

(56) References Cited

U.S. PATENT DOCUMENTS

2011/0276020 A1 11/2011 Mitsui
2012/0004079 A1 1/2012 Hyacinth
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1 5/2012 Wheaton et al.
2012/0116336 A1 5/2012 Sharma et al.
2012/0137420 A1 6/2012 Gordon et al.
2012/0165768 A1 6/2012 Sekiyama et al.
2012/0165786 A1 6/2012 Chappa et al.
2012/0209216 A1 8/2012 Jensen et al.
2012/0209225 A1 8/2012 Hu et al.
2012/0210503 A1 8/2012 Anzivino et al.
2012/0215187 A1 8/2012 Tippet et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.
2012/0253303 A1 10/2012 Suzuki et al.
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1 1/2013 Wada et al.
2013/0019374 A1 1/2013 Schwartz
2013/0036544 A1 2/2013 Lee et al.
2013/0045651 A1 2/2013 Esteves et al.
2013/0046258 A1 2/2013 Chambers
2013/0053804 A1 2/2013 Soerensen et al.
2013/0096523 A1 4/2013 Chang et al.
2013/0110059 A1 5/2013 Kossow et al.
2013/0138064 A1 5/2013 Stroebech et al.
2013/0144240 A1 6/2013 Ellis
2013/0150813 A1 6/2013 Gordon et al.
2013/0158494 A1 6/2013 Ong et al.
2013/0165880 A1 6/2013 Amos et al.
2013/0211385 A1 8/2013 Lazarus
2013/0218112 A1 8/2013 Thompson
2013/0245496 A1 9/2013 Wells et al.
2013/0245586 A1 9/2013 Jha
2013/0253528 A1 9/2013 Haffner et al.
2013/0274711 A1* 10/2013 O'Day .................. A61M 39/08 604/508
2013/0292537 A1 11/2013 Dirico
2013/0324954 A1 12/2013 Friedrich
2013/0330501 A1 12/2013 Aizenberg et al.
2014/0005647 A1 1/2014 Shuffler et al.
2014/0031774 A1 1/2014 Bengtson
2014/0039432 A1 2/2014 Dunbar et al.
2014/0039440 A1 2/2014 Doescher
2014/0058347 A1 2/2014 Marquette
2014/0107595 A1 4/2014 Blott et al.
2014/0107599 A1 4/2014 Fink et al.
2014/0157499 A1 6/2014 Suzuki et al.
2014/0171889 A1 6/2014 Hopman et al.
2014/0182051 A1 7/2014 Tanimoto et al.
2014/0196189 A1 7/2014 Lee et al.
2014/0216478 A1 8/2014 Park et al.
2014/0230831 A1 8/2014 Zaltsberg et al.
2014/0257231 A1 9/2014 Wang et al.
2014/0276501 A1 9/2014 Cisko
2014/0303582 A1 10/2014 Wright et al.
2014/0316381 A1 10/2014 Reglin
2014/0325746 A1 11/2014 Block
2014/0343516 A1 11/2014 Coulthard et al.
2014/0348139 A1 11/2014 Gomez Martinez
2014/0352050 A1 12/2014 Yao et al.
2014/0371628 A1 12/2014 Desai
2015/0045757 A1 2/2015 Lee et al.
2015/0047114 A1 2/2015 Ramirez
2015/0048089 A1 2/2015 Robertson
2015/0135423 A1 5/2015 Sharpe et al.
2015/0157300 A1 6/2015 Ealovega et al.
2015/0209188 A1 7/2015 Scheremet et al.
2015/0209194 A1 7/2015 Heyman
2015/0216714 A1 8/2015 Sasaki et al.
2015/0238687 A1 8/2015 Novakovic et al.
2015/0267862 A1 9/2015 Mishler
2015/0290421 A1* 10/2015 Glickman ........... A61M 25/003 604/30
2015/0290425 A1 10/2015 Macy et al.
2015/0320583 A1 11/2015 Harvie
2015/0329255 A1 11/2015 Rzepecki
2015/0342799 A1 12/2015 Michiels et al.
2015/0359660 A1 12/2015 Harvie
2015/0359996 A1 12/2015 Arora et al.
2015/0366699 A1 12/2015 Nelson
2015/0374535 A1 12/2015 Davis et al.
2016/0008193 A1 1/2016 Schulke
2016/0029998 A1 2/2016 Brister et al.
2016/0030228 A1 2/2016 Jones
2016/0038356 A1 2/2016 Yao et al.
2016/0051395 A1 2/2016 Ugarte M.D.
2016/0058322 A1 3/2016 Brister et al.
2016/0060001 A1 3/2016 Wada et al.
2016/0100976 A1 4/2016 Conway et al.
2016/0106604 A1 4/2016 Timm
2016/0113809 A1 4/2016 Kim
2016/0135792 A1 5/2016 Cai
2016/0136338 A1 5/2016 Lee et al.
2016/0183689 A1 6/2016 Miner
2016/0256022 A1 9/2016 Le
2016/0270982 A1 9/2016 Raycheck et al.
2016/0278662 A1 9/2016 Brister et al.
2016/0327553 A1 11/2016 Edwards et al.
2016/0357400 A1 12/2016 Penha et al.
2016/0366699 A1 12/2016 Zhang et al.
2016/0367226 A1 12/2016 Newton et al.
2016/0367411 A1 12/2016 Justiz et al.
2016/0367726 A1 12/2016 Gratzer
2016/0374848 A1 12/2016 Sanchez et al.
2017/0007438 A1 1/2017 Harvie
2017/0014560 A1 1/2017 Minskoff et al.
2017/0028110 A1 2/2017 Smith et al.
2017/0042724 A1 2/2017 Ugarte
2017/0042748 A1 2/2017 Griffin
2017/0049605 A1 2/2017 Wisniewski
2017/0100276 A1 4/2017 Joh
2017/0107312 A1 4/2017 Hinayama et al.
2017/0128638 A1 5/2017 Giezendanner et al.
2017/0136209 A1 5/2017 Burnett et al.
2017/0143534 A1 5/2017 Sanchez
2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1 9/2017 Sanchez et al.
2017/0266658 A1 9/2017 Bruno et al.
2017/0281399 A1 10/2017 Vanmiddendorp et al.
2017/0281419 A1 10/2017 Pintado
2017/0312116 A1 11/2017 Laniado
2017/0312405 A1 11/2017 Newton
2017/0325788 A1 11/2017 Ealovega et al.
2017/0333244 A1 11/2017 Laniado
2017/0340489 A1 11/2017 Yamada
2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1 2/2018 Newton et al.
2018/0037384 A1 2/2018 Archeny et al.
2018/0049910 A1 2/2018 Newton
2018/0064572 A1 3/2018 Wiltshire

(56) References Cited

U.S. PATENT DOCUMENTS

| | | | |
|---|---|---|---|
| 2018/0104131 | A1 | 4/2018 | Killian |
| 2018/0127187 | A1 | 5/2018 | Sewell |
| 2018/0149635 | A1 | 5/2018 | Abir |
| 2018/0169281 | A1 | 6/2018 | Russell et al. |
| 2018/0193215 | A1 | 7/2018 | Davies et al. |
| 2018/0200101 | A1 | 7/2018 | Su |
| 2018/0214297 | A1 | 8/2018 | Hughett et al. |
| 2018/0215649 | A1 | 8/2018 | Wada et al. |
| 2018/0221216 | A1 | 8/2018 | Benz et al. |
| 2018/0228642 | A1 | 8/2018 | Davis et al. |
| 2018/0229014 | A1 | 8/2018 | Guirguis et al. |
| 2018/0256384 | A1 | 9/2018 | Kasirye |
| 2018/0271694 | A1 | 9/2018 | Fernandez et al. |
| 2018/0280236 | A1 | 10/2018 | Ludin et al. |
| 2018/0317892 | A1 | 11/2018 | Catlin |
| 2018/0325748 | A1 | 11/2018 | Sharma et al. |
| 2019/0001029 | A1 | 1/2019 | Davie et al. |
| 2019/0001030 | A1 | 1/2019 | Braga et al. |
| 2019/0021899 | A1 | 1/2019 | Vlet |
| 2019/0029869 | A1 | 1/2019 | Huchthausen |
| 2019/0038451 | A1 | 2/2019 | Harvie |
| 2019/0046102 | A1 | 2/2019 | Kushnir et al. |
| 2019/0059938 | A1 | 2/2019 | Holsten |
| 2019/0060138 | A1 | 2/2019 | Marquez et al. |
| 2019/0091059 | A1 | 3/2019 | Gabriel |
| 2019/0100362 | A1 | 4/2019 | Meyers et al. |
| 2019/0133126 | A1 | 5/2019 | Modak et al. |
| 2019/0133814 | A1 | 5/2019 | Tammen et al. |
| 2019/0142624 | A1* | 5/2019 | Sanchez ................ A61D 99/00 604/319 |
| 2019/0224036 | A1 | 7/2019 | Sanchez et al. |
| 2019/0226189 | A1 | 7/2019 | Braxton |
| 2019/0240079 | A1 | 8/2019 | Tuli |
| 2019/0247222 | A1 | 8/2019 | Ecklund et al. |
| 2019/0247223 | A1 | 8/2019 | Brun et al. |
| 2019/0247623 | A1 | 8/2019 | Helm et al. |
| 2019/0282391 | A1 | 9/2019 | Johannes et al. |
| 2019/0314189 | A1 | 10/2019 | Acosta |
| 2019/0314190 | A1 | 10/2019 | Sanchez et al. |
| 2019/0321587 | A1 | 10/2019 | Mcmenamin et al. |
| 2019/0344934 | A1 | 11/2019 | Faerber et al. |
| 2019/0365303 | A1 | 12/2019 | Bullington et al. |
| 2019/0365307 | A1 | 12/2019 | Laing et al. |
| 2019/0365561 | A1 | 12/2019 | Newton et al. |
| 2019/0374373 | A1 | 12/2019 | Joh |
| 2020/0008985 | A1 | 1/2020 | Nguyen et al. |
| 2020/0016012 | A1 | 1/2020 | Dutkiewicz |
| 2020/0030595 | A1 | 1/2020 | Boukidjian et al. |
| 2020/0040561 | A1 | 2/2020 | Sugawara |
| 2020/0046544 | A1 | 2/2020 | Godinez et al. |
| 2020/0055638 | A1 | 2/2020 | Lau et al. |
| 2020/0070392 | A1 | 3/2020 | Huber et al. |
| 2020/0085609 | A1 | 3/2020 | Schelch et al. |
| 2020/0085610 | A1 | 3/2020 | Cohn et al. |
| 2020/0086090 | A1 | 3/2020 | Von Weymarn-Schärli et al. |
| 2020/0107518 | A1 | 4/2020 | Hiroshima et al. |
| 2020/0129322 | A1 | 4/2020 | Leuckel |
| 2020/0171217 | A9 | 6/2020 | Braga et al. |
| 2020/0179177 | A1 | 6/2020 | Erdem et al. |
| 2020/0187918 | A1 | 6/2020 | Wiygul |
| 2020/0206015 | A1 | 7/2020 | Langer |
| 2020/0206039 | A1 | 7/2020 | Mclain |
| 2020/0214910 | A1 | 7/2020 | Varona et al. |
| 2020/0216898 | A1 | 7/2020 | Hubbell |
| 2020/0216989 | A1 | 7/2020 | Kinugasa et al. |
| 2020/0229964 | A1 | 7/2020 | Staali et al. |
| 2020/0231343 | A1 | 7/2020 | Freedman et al. |
| 2020/0232841 | A1 | 7/2020 | Satish et al. |
| 2020/0246172 | A1 | 8/2020 | Ho |
| 2020/0246203 | A1 | 8/2020 | Tulk et al. |
| 2020/0255189 | A1 | 8/2020 | Liu |
| 2020/0261280 | A1 | 8/2020 | Heyman |
| 2020/0276046 | A1 | 9/2020 | Staali et al. |
| 2020/0306075 | A1 | 10/2020 | Newton et al. |
| 2020/0315837 | A1 | 10/2020 | Radl et al. |
| 2020/0315838 | A1 | 10/2020 | Eckert |
| 2020/0315872 | A1 | 10/2020 | Viens et al. |
| 2020/0315874 | A1 | 10/2020 | Viens et al. |
| 2020/0331672 | A1 | 10/2020 | Bertram et al. |
| 2020/0345332 | A1 | 11/2020 | Duval |
| 2020/0352774 | A1 | 11/2020 | Rabinowitz et al. |
| 2020/0353135 | A1 | 11/2020 | Gregory et al. |
| 2020/0367677 | A1 | 11/2020 | Silsby et al. |
| 2020/0369444 | A1 | 11/2020 | Silsby et al. |
| 2020/0375781 | A1 | 12/2020 | Staali et al. |
| 2020/0375810 | A1 | 12/2020 | Carlin et al. |
| 2020/0384242 | A1 | 12/2020 | Havard et al. |
| 2020/0385179 | A1 | 12/2020 | McCourt |
| 2020/0390591 | A1 | 12/2020 | Glithero et al. |
| 2020/0390592 | A1 | 12/2020 | Merrill |
| 2020/0398024 | A1 | 12/2020 | Fletter et al. |
| 2020/0405521 | A1 | 12/2020 | Glasroe |
| 2020/0405523 | A1 | 12/2020 | Obst et al. |
| 2021/0007910 | A1 | 1/2021 | Furukawa |
| 2021/0008771 | A1 | 1/2021 | Huber et al. |
| 2021/0009323 | A1 | 1/2021 | Markarian et al. |
| 2021/0020072 | A1 | 1/2021 | Moehring et al. |
| 2021/0023279 | A1 | 1/2021 | Radl et al. |
| 2021/0059853 | A1 | 3/2021 | Davis et al. |
| 2021/0061523 | A1 | 3/2021 | Bytheway |
| 2021/0069005 | A1 | 3/2021 | Sanchez et al. |
| 2021/0069008 | A1 | 3/2021 | Blabas et al. |
| 2021/0069009 | A1 | 3/2021 | Im |
| 2021/0069030 | A1 | 3/2021 | Nishikawa et al. |
| 2021/0077993 | A1 | 3/2021 | Nazareth et al. |
| 2021/0113749 | A1 | 4/2021 | Radl et al. |
| 2021/0121318 | A1 | 4/2021 | Pinlac |
| 2021/0137724 | A1 | 5/2021 | Ecklund et al. |
| 2021/0138190 | A1 | 5/2021 | Erbey et al. |
| 2021/0154055 | A1 | 5/2021 | Villarreal |
| 2021/0170079 | A1 | 6/2021 | Radl et al. |
| 2021/0178390 | A1 | 6/2021 | Oueslati et al. |
| 2021/0186742 | A1 | 6/2021 | Newton et al. |
| 2021/0186744 | A1 | 6/2021 | Spector |
| 2021/0206144 | A1 | 7/2021 | Ewell |
| 2021/0211568 | A1 | 7/2021 | Zhou et al. |
| 2021/0212865 | A1 | 7/2021 | Wallajapet et al. |
| 2021/0220162 | A1 | 7/2021 | Jamison |
| 2021/0220163 | A1 | 7/2021 | Mayrand |
| 2021/0228400 | A1 | 7/2021 | Glithero |
| 2021/0228401 | A1 | 7/2021 | Becker et al. |
| 2021/0228795 | A1 | 7/2021 | Hughett et al. |
| 2021/0229877 | A1 | 7/2021 | Ragias et al. |
| 2021/0236323 | A1 | 8/2021 | Austermann et al. |
| 2021/0236324 | A1 | 8/2021 | Sweeney |
| 2021/0251814 | A1 | 8/2021 | Jönegren et al. |
| 2021/0267787 | A1 | 9/2021 | Nazemi |
| 2021/0275343 | A1 | 9/2021 | Sanchez et al. |
| 2021/0275344 | A1 | 9/2021 | Wing |
| 2021/0290454 | A1 | 9/2021 | Yamada |
| 2021/0290464 | A1 | 9/2021 | Furuta |
| 2021/0315726 | A1 | 10/2021 | Lin |
| 2021/0315727 | A1 | 10/2021 | Jiang |
| 2021/0353449 | A1 | 11/2021 | Sharma et al. |
| 2021/0353450 | A1 | 11/2021 | Sharma et al. |
| 2021/0361469 | A1 | 11/2021 | Liu et al. |
| 2021/0369495 | A1 | 12/2021 | Cheng et al. |
| 2021/0386925 | A1 | 12/2021 | Hartwell et al. |
| 2021/0393433 | A1 | 12/2021 | Godinez et al. |
| 2022/0015958 | A1 | 1/2022 | Ito |
| 2022/0023091 | A1 | 1/2022 | Ecklund et al. |
| 2022/0026546 | A1 | 1/2022 | Aono et al. |
| 2022/0031290 | A1 | 2/2022 | Weed |
| 2022/0031523 | A1 | 2/2022 | Pierpoint |
| 2022/0039995 | A1 | 2/2022 | Johannes et al. |
| 2022/0047410 | A1 | 2/2022 | Walthall |
| 2022/0062025 | A1 | 3/2022 | Shields et al. |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |

(56) References Cited

U.S. PATENT DOCUMENTS

| | | | |
|---|---|---|---|
| 2022/0104976 | A1 | 4/2022 | Hoeger et al. |
| 2022/0104981 | A1 | 4/2022 | Jones |
| 2022/0117773 | A1 | 4/2022 | Davis et al. |
| 2022/0117774 | A1 | 4/2022 | Meyer et al. |
| 2022/0117775 | A1 | 4/2022 | Jones et al. |
| 2022/0118165 | A1 | 4/2022 | Knapp et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0168159 | A1 | 6/2022 | Triado et al. |
| 2022/0193312 | A1 | 6/2022 | Lee et al. |
| 2022/0211536 | A1 | 7/2022 | Johannes et al. |
| 2022/0218510 | A1 | 7/2022 | Metzger et al. |
| 2022/0229053 | A1 | 7/2022 | Levin et al. |
| 2022/0241106 | A1 | 8/2022 | Johannes et al. |
| 2022/0241115 | A1 | 8/2022 | Lang et al. |
| 2022/0247407 | A1 | 8/2022 | Yamamoto et al. |
| 2022/0248836 | A1 | 8/2022 | Cagle et al. |
| 2022/0257407 | A1 | 8/2022 | Johannes et al. |
| 2022/0265460 | A1 | 8/2022 | Coker |
| 2022/0265462 | A1 | 8/2022 | Alder et al. |
| 2022/0270711 | A1 | 8/2022 | Feala et al. |
| 2022/0273482 | A1 | 9/2022 | Johannes et al. |
| 2022/0280357 | A1 | 9/2022 | Jagannathan et al. |
| 2022/0280710 | A1 | 9/2022 | Agrawal et al. |
| 2022/0287689 | A1 | 9/2022 | Johannes |
| 2022/0287691 | A1 | 9/2022 | Wormser et al. |
| 2022/0287867 | A1 | 9/2022 | Jones et al. |
| 2022/0287868 | A1 | 9/2022 | Garvey et al. |
| 2022/0296408 | A1 | 9/2022 | Evans et al. |
| 2022/0305191 | A1 | 9/2022 | Joseph et al. |
| 2022/0313222 | A1 | 10/2022 | Austermann et al. |
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Yin et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0180737 | A1 | 6/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0335599 | A1 | 10/2024 | Cheng et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |
| 2026/0020972 | A1 | 1/2026 | Godinez et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 2488867 | C | 8/2007 |
| CA | 3031934 | A1 | 2/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 2569779 | Y | 9/2003 |
| CN | 1533755 | A | 10/2004 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |

(56) References Cited

FOREIGN PATENT DOCUMENTS

| | | | |
|---|---|---|---|
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451607 | A | 3/2016 |
| CN | 105451693 | A | 3/2016 |
| CN | 105534632 | A | 5/2016 |
| CN | 105616072 | A | 6/2016 |
| CN | 106132360 | A | 11/2016 |
| CN | 106137631 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 207785556 | U | 8/2018 |
| CN | 110171118 | A | 8/2019 |
| CN | 209285902 | U | 8/2019 |
| CN | 110381883 | A | 10/2019 |
| CN | 111465375 | A | 7/2020 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 3104356 | A1 | 9/1982 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 202006018506 | U1 | 3/2007 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0945231 | A2 | 9/1999 |
| EP | 0966936 | A1 | 12/1999 |
| EP | 0987293 | A1 | 3/2000 |
| EP | 1063953 | A1 | 1/2001 |

| | | | |
|---|---|---|---|
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| FR | 2294812 | A1 | 7/1976 |
| FR | 2826704 | A1 | 1/2003 |
| GB | 871820 | A | 7/1961 |
| GB | 873045 | A | 7/1961 |
| GB | 996370 | A | 6/1965 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |

(56) References Cited

FOREIGN PATENT DOCUMENTS

| | | | |
|---|---|---|---|
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022536986 | A | 8/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20100137210 | A | 12/2010 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 20180106659 | A | 10/2018 |
| KR | 20180108774 | A | 10/2018 |
| KR | 101976679 | B1 | 5/2019 |
| KR | 101998130 | B1 | 7/2019 |
| KR | 20230034343 | A | 3/2023 |
| PT | 2068717 | E | 6/2013 |
| SE | 505542 | C2 | 9/1997 |
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |

(56) References Cited

FOREIGN PATENT DOCUMENTS

| | | | |
|---|---|---|---|
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018200721 | A1 | 11/2018 |
| WO | 2018235026 | A1 | 12/2018 |
| WO | 2018235065 | A1 | 12/2018 |
| WO | 2019004404 | A1 | 1/2019 |
| WO | 2019038732 | A1 | 2/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |

(56) References Cited

FOREIGN PATENT DOCUMENTS

| | | | |
|---|---|---|---|
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.

(56) References Cited

OTHER PUBLICATIONS

Final Office Action for U.S. Appl. No. 15/612,325 mailed Sep. 17, 2020.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.

(56) References Cited

OTHER PUBLICATIONS

International Search Report and Written Opinion from International Application No. PCT/US2022/012794 mailed May 3, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 17/662,700 mailed Jul. 22, 2022.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Aug. 5, 2021.
Notice of Allowance for U.S. Appl. No. 17/088,272 mailed Mar. 4, 2022.

(56) References Cited

OTHER PUBLICATIONS

Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.

(56) References Cited

OTHER PUBLICATIONS

U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.

(56) References Cited

OTHER PUBLICATIONS

"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
MaCaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
PureWick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/452,258 mailed Oct. 26, 2022.
Advisory Action for U.S. Appl. No. 16/478,180 mailed Sep. 21, 2022.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2021/039866 mailed Oct. 7, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015781 mailed May 6, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/034457 mailed Oct. 12, 2022.
Issue Notification for U.S. Appl. No. 16,905,400 mailed Nov. 30, 2022.
Notice of Allowance for U.S. Appl. No. 16/899,956 mailed Dec. 1, 2022.
Notice of Allowance for U.S. Appl. No. 17/461,036 mailed Oct. 6, 2022.
U.S. Appl. No. 15/384,196, filed Dec. 19, 2016.
U.S. Appl. No. 17/907,125, filed Sep. 23, 2022.
U.S. Appl. No. 17/912,147, filed Sep. 16, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 62/991,754, filed Mar. 19, 2020.
U.S. Appl. No. 63/241,328, filed Sep. 7, 2021.
Advisory Action for U.S. Appl. No. 16/452,258 mailed May 5, 2025.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Feb. 28, 2025.
Advisory Action for U.S. Appl. No. 17/451,345 mailed Jul. 3, 2024.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,314 mailed Apr. 8, 2025.

(56) References Cited

OTHER PUBLICATIONS

Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/140,163 mailed Jun. 3, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 17/907,125 mailed Apr. 30, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/036875 mailed May 31, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077205 mailed Jul. 19, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/646,771 mailed Mar. 19, 2025.
Issue Notification for U.S. Appl. No. 17/657,474 mailed Jun. 19, 2024.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/663,330 mailed Feb. 26, 2025.
Issue Notification for U.S. Appl. No. 17/664,914 mailed Nov. 6, 2024.

(56) References Cited

OTHER PUBLICATIONS

Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/051,600 mailed Feb. 28, 2025.
Non-Final Office Action for U.S. Appl. No. 17/378,015 mailed Jul. 5, 2024.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/446,654 mailed May 1, 2025.
Non-Final Office Action for U.S. Appl. No. 17/451,345 mailed Jul. 25, 2024.
Non-Final Office Action for U.S. Appl. No. 17/451,354 mailed Mar. 19, 2025.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/645,821 mailed Sep. 6, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/655,464 mailed Mar. 20, 2025.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/757,311 mailed Oct. 22, 2024.
Non-Final Office Action for U.S. Appl. No. 17/758,152 mailed Apr. 8, 2025.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/907,125 mailed Dec. 13, 2024.
Non-Final Office Action for U.S. Appl. No. 17/996,064 mailed Mar. 6, 2025.
Non-Final Office Action for U.S. Appl. No. 18/003,029 mailed Apr. 18, 2025.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Apr. 25, 2025.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/444,792 mailed Mar. 28, 2025.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.

(56) References Cited

OTHER PUBLICATIONS

Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 17/758,316 mailed Mar. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,468 mailed Apr. 14, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/755,236 mailed Apr. 24, 2025.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/930,238 mailed Apr. 17, 2025.
Supplemental Notice of Allowance for U.S. Appl. No. 17/597,673 mailed Apr. 10, 2025.
U.S. Appl. No. 17/013,822, filed Sep. 7, 2020.
U.S. Appl. No. 17/596,629, filed Dec. 15, 2021.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/171,983, filed Apr. 7, 2025.
U.S. Appl. No. 19/179,540, filed Apr. 15, 2025.
U.S. Appl. No. 63,564,696, filed Mar. 13, 2024.
U.S. Appl. No. 63/181,709, filed Apr. 29, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
Martin, "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.

(56) References Cited

OTHER PUBLICATIONS

Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/139,523 mailed Apr. 24, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2022/015026 mailed Oct. 31, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.
International Search Report and Written Opinion from International Application No. PCT/US2022/032424 mailed Oct. 11, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.

(56) References Cited

OTHER PUBLICATIONS

International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/450,864 mailed May 29, 2024.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Apr. 24, 2024.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.

(56) References Cited

OTHER PUBLICATIONS

Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/661,090 mailed May 22, 2024.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109 filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.

(56) References Cited

OTHER PUBLICATIONS

U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Decibel", https://web.archive.org/web/20200415219l7/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
"Surface Energy Data for Cellulose acetate, CAS # 9004-35-7", Diviersified Enterprises, 2009, 1 page.
"Tube Definition & Meaning" Merriam Webster Dictionary, 2025, <https://www.merriam-webster.com/dictionary/tube>.
Advisory Action for U.S. Appl. No. 17/378,015 mailed Oct. 28, 2025.
Advisory Action for U.S. Appl. No. 17/446,256 mailed Nov. 6, 2025.
Advisory Action for U.S. Appl. No. 17/450,864 mailed Mar. 21, 2024.
Advisory Action for U.S. Appl. No. 17/451,345 mailed May 13, 2025.
Advisory Action for U.S. Appl. No. 17/757,311 mailed Jul. 2, 2025.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/808,354 mailed Nov. 25, 2025.
Corrected Notice of Allowability for U.S. Appl. No. 18/260,122 mailed Aug. 11, 2025.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/614,173 mailed May 20, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 18/003,029 mailed Nov. 26, 2025.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/265,736 mailed Dec. 1, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 17/444,792 mailed Jun. 25, 2025.
Issue Notification for U.S. Appl. No. 17/597,673 mailed Jun. 4, 2025.
Issue Notification for U.S. Appl. No. 17/653,920 mailed Oct. 22, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/996,064 mailed Nov. 5, 2025.
Issue Notification for U.S. Appl. No. 17/996,155 mailed Oct. 8, 2025.

(56) References Cited

OTHER PUBLICATIONS

Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/134,857 mailed May 28, 2025.
Issue Notification for U.S. Appl. No. 18/260,122 mailed Nov. 12, 2025.
Non-Final Office Action for U.S. Appl. No. 16/452,258 mailed Sep. 24, 2025.
Non-Final Office Action for U.S. Appl. No. 17/378,015 mailed Dec. 12, 2025.
Non-Final Office Action for U.S. Appl. No. 17/446,256 mailed Dec. 2, 2025.
Non-Final Office Action for U.S. Appl. No. 17/595,747 mailed Jun. 12, 2025.
Non-Final Office Action for U.S. Appl. No. 17/628,411 mailed Dec. 22, 2025.
Non-Final Office Action for U.S. Appl. No. 17/635,866 mailed Jul. 29, 2025.
Non-Final Office Action for U.S. Appl. No. 17/653,314 mailed May 8, 2025.
Non-Final Office Action for U.S. Appl. No. 17/664,487 mailed May 19, 2025.
Non-Final Office Action for U.S. Appl. No. 17/759,697 mailed Sep. 17, 2025.
Non-Final Office Action for U.S. Appl. No. 17/912,147 mailed May 29, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,556 mailed Dec. 22, 2025.
Non-Final Office Action for U.S. Appl. No. 18/006,807 mailed May 29, 2025.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jul. 11, 2025.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/548,152 mailed Sep. 16, 2025.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/757,964 mailed Aug. 20, 2025.
Notice of Allowance for U.S. Appl. No. 16/433,773 mailed Oct. 10, 2025.
Notice of Allowance for U.S. Appl. No. 17/051,399 mailed Nov. 17, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed May 27, 2025.
Notice of Allowance for U.S. Appl. No. 17/625,941 mailed Nov. 13, 2025.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/755,236 mailed Jul. 17, 2025.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,253 mailed Jul. 11, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/044,413 mailed Sep. 16, 2025.
Notice of Allowance for U.S. Appl. No. 18/260,122 mailed Jul. 30, 2025.
Restriction Requirement for U.S. Appl. No. 17/625,887 mailed Sep. 2, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/294,370 mailed Nov. 26, 2025.
Restriction Requirement for U.S. Appl. No. 18/335,579 mailed Nov. 26, 2025.
Restriction Requirement for U.S. Appl. No. 18/373,424 mailed Nov. 14, 2025.

(56) References Cited

OTHER PUBLICATIONS

Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/662,216 mailed Nov. 26, 2025.
Restriction Requirement for U.S. Appl. No. 19/237,638 mailed Dec. 18, 2025.
U.S. Appl. No. 18/034,902, filed May 2, 2023.
U.S. Appl. No. 18/951,944, filed Nov. 19, 2024.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/491,481, filed Dec. 9, 2025.
U.S. Appl. No. 19/494,631, filed Dec. 18, 2025.
"Proximate Definition & Meaning" <https://www.merriam-webster.com/dictionary/> 2025.
Advisory Action for U.S. Appl. No. 16/452,258 mailed Apr. 17, 2026.
Advisory Action for U.S. Appl. No. 17/394,055 mailed Jan. 9, 2026.
Advisory Action for U.S. Appl. No. 17/446,654 mailed Apr. 16, 2026.
Advisory Action for U.S. Appl. No. 17/664,487 mailed Apr. 9, 2026.
Advisory Action for U.S. Appl. No. 18/006,807 mailed May 4, 2026.
Advisory Action for U.S. Appl. No. 18/042,842 mailed Apr. 14, 2026.
Advisory Action for U.S. Appl. No. 18/164,800 mailed Apr. 9, 2026.
Advisory Action for U.S. Appl. No. 18/247,986 mailed Apr. 1, 2026.
Advisory Action for U.S. Appl. No. 18/265,736 mailed Mar. 4, 2026.
Corrected Notice of Allowability for U.S. Appl. No. 17/754,736 mailed Feb. 12, 2026.
Corrected Notice of Allowability for U.S. Appl. No. 18/041,109 mailed Apr. 2, 2026.
Corrected Notice of Allowability for U.S. Appl. No. 18/249,577 mailed Apr. 15, 2026.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Corrected Notice of Allowability for U.S. Appl. No. 18/294,370 mailed Mar. 31, 2026.
Final Office Action for U.S. Appl. No. 16/452,258 mailed Feb. 11, 2026.
Final Office Action for U.S. Appl. No. 17/595,747 mailed Feb. 19, 2026.
Final Office Action for U.S. Appl. No. 17/628,411 mailed Apr. 7, 2026.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/758,152 mailed Apr. 7, 2026.
Final Office Action for U.S. Appl. No. 17/809,083 mailed Jan. 23, 2026.
Final Office Action for U.S. Appl. No. 17/933,590 mailed Feb. 19, 2026.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/150,360 mailed Apr. 10, 2026.
Final Office Action for U.S. Appl. No. 18/247,986 mailed Jan. 7, 2026.
Final Office Action for U.S. Appl. No. 18/254,638 mailed Apr. 8, 2026.
Final Office Action for U.S. Appl. No. 18/548,152 mailed Apr. 15, 2026.
International Search Report and Written Opinion from International Application No. PCT/US2025/035383 mailed Oct. 10, 2025.
Issue Notification for U.S. Appl. No. 16/433,773 mailed Jan. 21, 2026.
Issue Notification for U.S. Appl. No. 17/051,399 mailed Mar. 4, 2026.
Issue Notification for U.S. Appl. No. 17/051,600 mailed Apr. 29, 2026.
Issue Notification for U.S. Appl. No. 17/451,354 mailed Feb. 25, 2026.
Issue Notification for U.S. Appl. No. 17/625,941 mailed Feb. 25, 2026.
Issue Notification for U.S. Appl. No. 17/645,821 mailed Apr. 1, 2026.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/759,697 mailed May 6, 2026.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 18/044,413 mailed Dec. 30, 2025.
Non-Final Office Action for U.S. Appl. No. 17/597,408 mailed Apr. 7, 2026.
Non-Final Office Action for U.S. Appl. No. 17/614,173 mailed Dec. 29, 2025.
Non-Final Office Action for U.S. Appl. No. 17/757,311 mailed Sep. 2, 2025.
Non-Final Office Action for U.S. Appl. No. 17/759,587 mailed Jan. 26, 2026.
Non-Final Office Action for U.S. Appl. No. 18/003,029 mailed Apr. 20, 2026.
Non-Final Office Action for U.S. Appl. No. 18/034,902 mailed Mar. 20, 2026.
Non-Final Office Action for U.S. Appl. No. 18/043,618 mailed May 1, 2026.
Non-Final Office Action for U.S. Appl. No. 18/043,807 mailed Feb. 10, 2026.
Non-Final Office Action for U.S. Appl. No. 18/246,121 mailed Jan. 22, 2026.
Non-Final Office Action for U.S. Appl. No. 18/259,626 mailed Jan. 30, 2026.
Non-Final Office Action for U.S. Appl. No. 18/260,391 mailed Apr. 29, 2026.
Non-Final Office Action for U.S. Appl. No. 18/260,394 mailed Jan. 13, 2026.
Non-Final Office Action for U.S. Appl. No. 18/263,800 mailed Feb. 5, 2026.
Non-Final Office Action for U.S. Appl. No. 18/335,579 mailed Apr. 24, 2026.

(56) References Cited

OTHER PUBLICATIONS

Non-Final Office Action for U.S. Appl. No. 18/376,274 mailed Mar. 9, 2026.
Non-Final Office Action for U.S. Appl. No. 18/546,465 mailed Apr. 1, 2026.
Non-Final Office Action for U.S. Appl. No. 18/549,387 mailed Mar. 4, 2026.
Non-Final Office Action for U.S. Appl. No. 18/551,492 mailed Mar. 19, 2026.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/569,711 mailed Mar. 30, 2026.
Non-Final Office Action for U.S. Appl. No. 18/569,778 mailed May 1, 2026.
Non-Final Office Action for U.S. Appl. No. 18/662,216 mailed Mar. 9, 2026.
Non-Final Office Action for U.S. Appl. No. 18/681,987 mailed Mar. 30, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Mar. 27, 2026.
Non-Final Office Action for U.S. Appl. No. 18/835,444 mailed Apr. 24, 2026.
Non-Final Office Action for U.S. Appl. No. 19/237,368 mailed Apr. 6, 2026.
Non-Final Office Action for U.S. Appl. No. 29/892,478 mailed Mar. 12, 2026.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/614,173 mailed May 7, 2026.
Notice of Allowance for U.S. Appl. No. 17/625,887 mailed Mar. 3, 2026.
Notice of Allowance for U.S. Appl. No. 17/635,866 mailed Mar. 2, 2026.
Notice of Allowance for U.S. Appl. No. 17/754,736 mailed Jan. 28, 2026.
Notice of Allowance for U.S. Appl. No. 17/757,311 mailed May 5, 2025.
Notice of Allowance for U.S. Appl. No. 17/759,697 mailed Jan. 30, 2026.
Notice of Allowance for U.S. Appl. No. 18/041,109 mailed Mar. 25, 2026.
Notice of Allowance for U.S. Appl. No. 18/249,577 mailed Mar. 31, 2026.
Notice of Allowance for U.S. Appl. No. 18/264,004 mailed Jan. 30, 2026.
Notice of Allowance for U.S. Appl. No. 18/264,278 mailed Apr. 24, 2026.
Notice of Allowance for U.S. Appl. No. 18/294,370 mailed Mar. 17, 2026.
Notice of Allowance for U.S. Appl. No. 18/553,625 mailed Apr. 15, 2026.
Notice of Allowance for U.S. Appl. No. 18/558,502 mailed May 6, 2026.
Notice of Allowance for U.S. Appl. No. 18/610,523 mailed Mar. 4, 2026.
Restriction Requirement for U.S. Appl. No. 18/260,394 mailed Jul. 25, 2025.
Restriction Requirement for U.S. Appl. No. 18/294,403 mailed Jan. 27, 2026.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/687,117 mailed Mar. 26, 2026.
U.S. Appl. No. 17/051,399, filed Oct. 28, 2020.
U.S. Appl. No. 17/625,941, filed Jan. 10, 2022.
U.S. Appl. No. 18/546,465, filed Aug. 15, 2023.
U.S. Appl. No. 19/353,151, filed Oct. 8, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.
U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.
U.S. Appl. No. 19/579,050, filed Apr. 16, 2026.
U.S. Appl. No. 19/582,525, filed Apr. 28, 2026.
U.S. Appl. No. 19/584,751, filed May 5, 2026.
U.S. Appl. No. 19/584,819, filed May 5, 2026.
U.S. Appl. No. 19/638,741, filed Apr. 3, 2026.
U.S. Appl. No. 19/657,823, filed Apr. 24, 2026.
U.S. Appl. No. 62/665,711, filed May 2, 2018.

* cited by examiner

FLUID COLLECTION WITH MULTIPORT VALVE ASSEMBLY

CROSS-REFERENCE TO RELATED APPLICATIONS

This application claims priority to U.S. Provisional Patent Application No. 63/241,328 filed on 7 Sep. 2021, the disclosure of which is incorporated herein, in its entirety, by this reference.

BACKGROUND

An individual may have limited or impaired mobility such that typical urination processes are challenging or impossible. For example, the individual may have surgery, a disability, or other medical condition that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, pressure ulcers spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments of the invention relate to fluid collection devices, system, and methods having a multiport valve assembly therein. In an embodiment, a fluid collection device is disclosed. The fluid collection device includes a fluid impermeable barrier at least partially defining an interior chamber and an opening through which the interior chamber is exposed to an external environment. The fluid collection device includes a fluid permeable body positioned at least partially within the interior chamber to extend across at least a portion of the opening and configured to wick fluid away from the opening. The fluid collection device includes a conduit extending into the interior chamber. The fluid collection device includes a multiport valve assembly disposed within the interior chamber.

In an embodiment, a fluid collection system is disclosed. The system includes a fluid collection device including a fluid impermeable barrier, a fluid permeable body, a conduit, and a multiport valve assembly. The system includes a fluid storage container fluidly connected to the fluid collection device via the conduit, the fluid storage container being configured to store fluids therein. The system includes a vacuum source fluidly connected to the fluid storage container, the vacuum source being configured to provide vacuum force into the interior chamber via the fluid storage container and the conduit.

In an embodiment, a method to collect bodily fluid is disclosed. The method includes positioning a fluid collection device including a fluid impermeable barrier, a fluid permeable body, a conduit, and a multiport valve assembly adjacent to a urethra of a wearer. The method includes receiving fluid from the urethra into the fluid collection device. The method includes removing the fluid from the fluid collection device via the conduit.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

Embodiments of the invention relate to fluid collection devices having a fluid impermeable barrier, a fluid permeable body, a conduit, and a multiport valve assembly as well as systems and methods for collecting fluid using the same.

The drawings illustrate several embodiments of the invention, wherein identical reference numerals refer to identical or similar elements or features in different views or embodiments shown in the drawings.

DETAILED DESCRIPTION

Embodiments disclosed herein relate to fluid collection devices designed to be placed near the urethra of a wearer and allow selection between a plurality of ports (e.g., valves) of a multiport valve assembly therein to collect fluid, such as urine, from the wearer and remove the fluid through one of the plurality of ports. Methods of using the fluid collection devices and systems including the fluid collection devices are also disclosed. Example fluid collection devices include a fluid impermeable barrier defining an interior chamber for collecting fluids. The fluid collection devices include a fluid permeable body at least partially disposed within the interior chamber. The fluid permeable body includes at least one permeable (e.g., porous) material for collecting and passing fluids therethrough, such as a wicking material (e.g., foam or spun plastic fibers). The fluid collection body may include a relatively soft fluid permeable membrane disposed over a fluid permeable support material, to interface with the flesh of a wearer. One or more of the fluid impermeable barrier or the fluid permeable body are sized and shaped to fit the wearer near the urethra such as one or more of over the vagina or between the legs of the wearer. The fluid collection devices include a multiport valve assembly within the interior chamber.

The multiport valve assembly allows a user (e.g., wearer, medical professional, etc.) to select a valve among a plurality of valves along a longitudinal length of the fluid collection device through which urine collected in the device is removed. Such a configuration allows for selective use of ports in different portions of the interior chamber based on the position of the wearer. For example, in a sitting position, fluid may pool in a medial portion of the interior chamber, whereas in a supine position or a reclined position, the fluid may pool in a second end region of the interior chamber.

Figure 1:
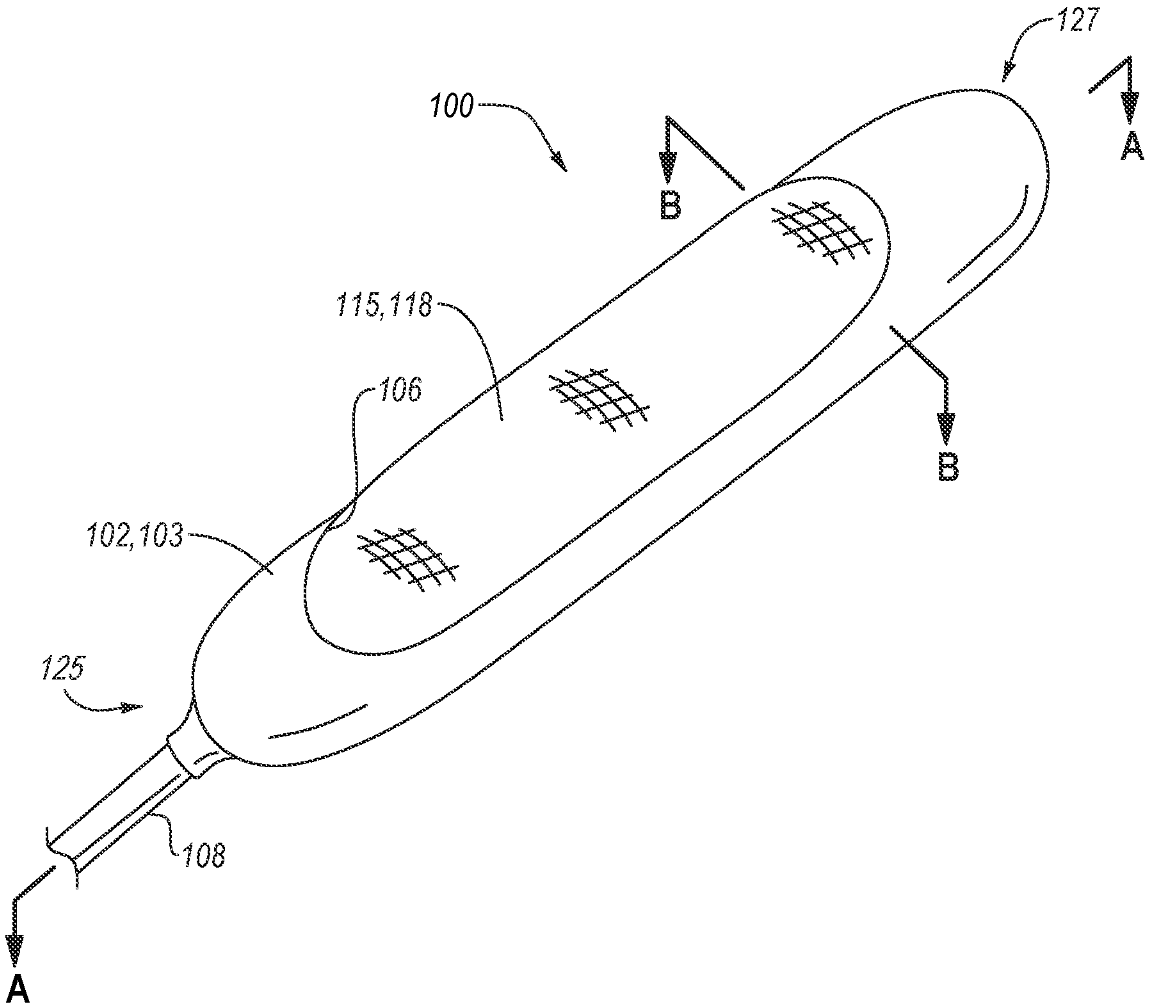
FIG. 1 is an isometric view of a fluid collection device, according to an embodiment.
Figure 2:
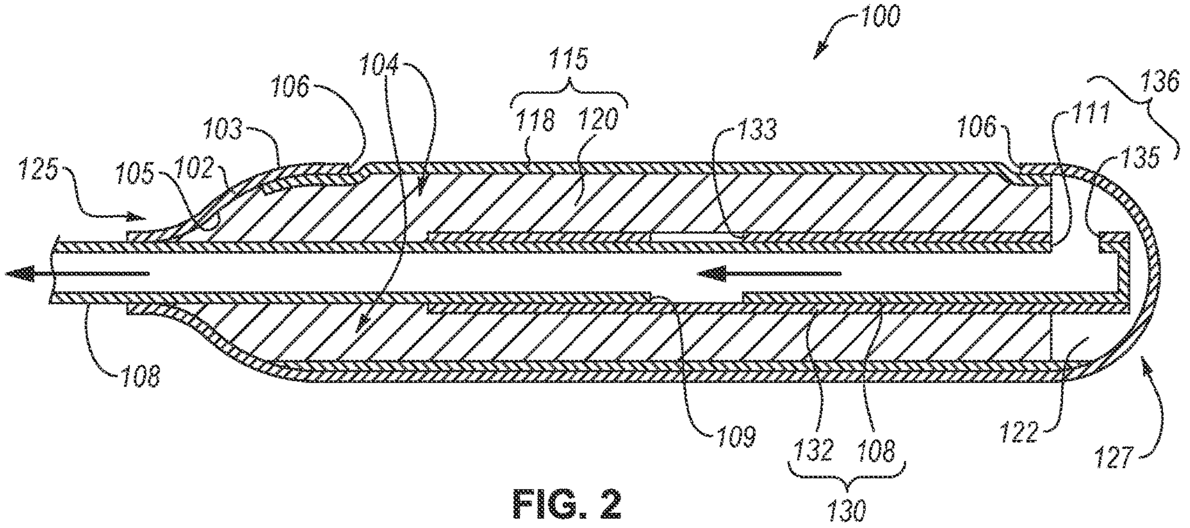
FIG. 2 is a cross-sectional view of the fluid collection device of FIG. 1 taken along the plane A-A.
Figure 3:
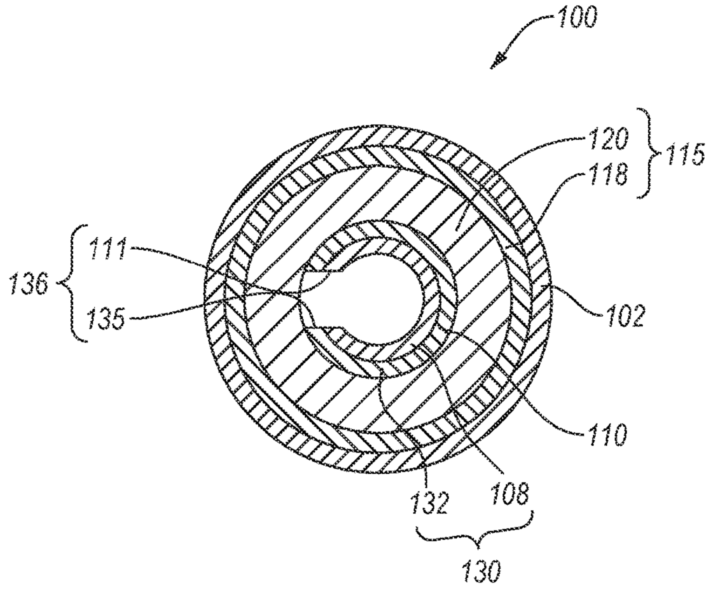
FIG. 3 is a cross-sectional view of the fluid collection device of FIG. 1 taken along the plane B-B.

FIG. 1 is an isometric view of a fluid collection device 100, according to an embodiment. FIG. 2 is a cross-sectional view of the fluid collection device 100 of FIG. 1 taken along the plane A-A. FIG. 3 is a cross-sectional view of the fluid collection device 100 of FIG. 1 taken along the plane B-B. The fluid collection device 100 is sized, shaped, and composed to collect urine from the urethra of a wearer. The fluid collection device 100 includes a fluid impermeable barrier 102 defining an interior chamber 104 therein, a fluid permeable body 115 disposed in the interior chamber 104, a conduit 108 disposed in the interior chamber 104, and a multiport valve assembly 130 disposed within the interior chamber 104. The multiport valve assembly 130 allows a user to select a port (e.g., valve formed from aligned holes) from a plurality of ports through which the urine is removed via the conduit 108. The fluid permeable body 115 may be exposed to the external environment via the opening 106 in the fluid impermeable barrier 102. During use, the fluid collection device 100 may be positioned over the urethra of the wearer and urine may be received into the fluid collection device 100 by the fluid permeable body 115 via the opening 106. The urine may be removed from the fluid collection device 100 via the conduit 108 disposed within the interior chamber 104 via one of the ports in the multiport valve assembly 130.

The fluid impermeable barrier 102 at least partially defines the interior chamber 104 and opening 106. For example, the inner surface(s) 105 of the fluid impermeable barrier 102 at least partially defines the interior chamber 104 within the fluid collection device 100. The fluid impermeable barrier 102 at least temporarily retains the fluid(s) in the interior chamber 104. The fluid impermeable barrier 102 may be formed of any suitable fluid impermeable material(s), such as a fluid impermeable polymer (e.g., silicone, polypropylene, polyethylene, polyethylene terephthalate, thermoplastic elastomer(s), a polycarbonate, etc.), a metal film, natural rubber, another suitable material, or combinations thereof. As such, the fluid impermeable barrier 102 substantially prevents the fluid(s) from passing therethrough. In an example, the fluid impermeable barrier 102 may be air permeable and liquid impermeable. In such an example, the fluid impermeable barrier 102 may be formed of a hydrophobic material that defines a plurality of pores that are air permeable but not liquid permeable. In an example, one or more portions of at least an outer surface of the fluid impermeable barrier 102 may be formed from a soft and/or smooth material, thereby reducing chaffing.

In some examples, the fluid impermeable barrier 102 may be tubular (ignoring the opening), such as substantially cylindrical, oblong, prismatic, a flattened tube, or any other extruded shape. The fluid impermeable barrier 102 may be sized and shaped to fit between the legs of a wearer. During use, an outer surface 103 of the fluid impermeable barrier 102 may at least partially contact the wearer, such as the thighs of the wearer.

The opening 106 provides an ingress route for fluids to enter the interior chamber 104. The opening 106 may be defined by the fluid impermeable barrier 102, such as by an inner edge of the fluid impermeable barrier 102. For example, the opening 106 is formed in and extends through the fluid impermeable barrier 102, from the outer surface 103 to the inner surface 105, thereby enabling fluid(s) to enter the interior chamber 104 from outside of the fluid collection device 100. The opening 106 may be located and shaped to be positioned adjacent to a wearer's urethra while the device is in use. At least a portion of porous material(s) of the fluid permeable body 115 disposed in the interior chamber 104 may be exposed through the opening 106 to allow fluids to move inwardly into the interior chamber 104, such as via one or more of permeation, suction, or wicking.

The fluid collection device 100 may be positioned proximate to the urethra and urine may enter the interior chamber 104 via the opening 106. When in use, the opening 106 may be elongated, extending from a first location below the urethra to a second location above the urethra (e.g., at or near the top of the vaginal opening or the pubic region). The opening 106 may exhibit an elongated shape because the space between the legs of a wearer is relatively narrow when the legs of the wearer are closed, thereby only permitting the flow of the fluid(s) along a path that corresponds to the elongated shape of the opening 106 (e.g., longitudinally extending opening).

The opening 106 in the fluid impermeable barrier 102 may exhibit a length that is measured along the longitudinal axis of the fluid collection device 100 that may be at least about 10% of the length of the fluid collection device 100, such as about 25% to about 50%, about 40% to about 60%, about 50% to about 75%, about 65% to about 85%, or about 75% to about 95% of the length of the fluid collection device 100. The opening 106 in the fluid impermeable barrier 102 may exhibit a width that is measured transverse to the longitudinal axis of the fluid collection device 100 and may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 may exhibit a width that is greater than 50% of the circumference of the fluid collection device 100 since the vacuum (e.g., suction) through the conduit 108 pulls the fluid through the fluid permeable body 115 and into the conduit 108. The opening 106 may be longitudinally oriented (e.g., having a major axis parallel to the longitudinal axis of the device 100). In some examples, the opening 106 may be laterally oriented (e.g., having a major axis perpendicular to the longitudinal axis of the device 100).

The fluid collection device 100 includes the fluid permeable body 115 disposed in the interior chamber 104. The fluid permeable body 115 may extend across at least a portion (e.g., all) of the opening 106. At least a portion of the fluid permeable body 115 may be exposed to an environment outside of the interior chamber 104 through the opening 106. The fluid permeable body 115 may wick and/or allow transport of any fluid away from the opening 106, thereby preventing the fluid from escaping the interior chamber 104.

The fluid permeable body 115 includes one or more porous materials. The fluid permeable body 115 may include one or more of a fluid permeable membrane 118 or a fluid permeable support 120. In some examples, the fluid permeable support 120 and the fluid permeable membrane 118 may be made of solely porous material(s). At least a portion of the porous material of the fluid permeable body 115 may be a wicking material configured to wick, draw, and/or allow transport any of the bodily fluids away from the opening 106, thereby preventing bodily fluids from escaping the interior chamber 104. The porous material may not include absorption of the bodily fluids into at least a portion of the porous material. Put another way, substantially no absorption or solubility of the bodily fluids into the porous material may take place after the porous material is exposed to the bodily fluids. While no absorption is desired, the term "substantially no absorption" may allow for nominal amounts of absorption and/or solubility of the bodily fluids into the porous material (e.g., absorbency), such as about 30 wt % of the dry weight of the porous material, about 20 wt %, about 10 wt %, about 7 wt %, about 5 wt %, about 3 wt %, about 2 wt %, about 1 wt %, or about 0.5 wt % of the dry weight of the porous material. In some examples, the porous material may include at least one absorbent or adsorbent material.

The fluid permeable membrane 118 may include any fluid permeable material that may wick the fluid. In some examples, the fluid permeable membrane 118 may be formed from a synthetic material such as polymer fibers or a natural material, such as cotton, wool, bamboo, silk, or combinations thereof. For example, the fluid permeable membrane 118 may include fabric, such as a gauze (e.g., a silk, linen, bamboo, or cotton gauze), another soft fabric, or another smooth fabric. The fluid permeable membrane 118 may include spun plastic fibers (e.g., nylon), such as a spun plastic mat or bed. Forming the fluid permeable membrane 118 from gauze, soft fabric, and/or smooth fabric may reduce chaffing caused by alternative materials.

The fluid permeable membrane 118 is disposed in the interior chamber 104. The fluid permeable membrane 118 may extend across at least a portion (e.g., all) of the opening 106. The fluid permeable membrane 118 may wick fluid inwardly away from the opening 106, thereby preventing fluid from escaping the interior chamber 104.

The fluid permeable body 115 may include the fluid permeable support 120 disposed in the interior chamber 104. The fluid permeable support 120 is positioned and composed to support the fluid permeable membrane 118 since the fluid permeable membrane 118 may be formed from a foldable, flimsy, or otherwise easily deformable material. For example, the fluid permeable support 120 may be positioned such that the fluid permeable membrane 118 is disposed between at least a portion of the fluid permeable support 120 and the fluid impermeable barrier 102. As such, the fluid permeable support 120 may support and maintain the position of the fluid permeable membrane 118 thereon. The fluid permeable support 120 may include any material that may wick the fluid, such as any of the fluid permeable membrane materials disclosed herein. For example, the fluid permeable support 120 may be formed from any fluid permeable material that is less deformable than the fluid permeable membrane 118, such as any of the materials disclosed herein for the fluid permeable membrane 118, in a more dense or rigid form. In some examples, the fluid permeable support 120 may include a porous polymer (e.g., nylon, polyester, polyurethane, polyethylene, polypropylene, etc.) structure, an open cell foam, or spun plastic fibers (e.g., nylon fibers). In some examples, the fluid permeable membrane 118 may include gauze and the fluid permeable support may include spun nylon fibers. In some examples, the fluid permeable support 120 may be formed from fabric, felt, gauze, or combinations thereof. In some examples, the fluid permeable support 120 may be formed from a natural material, such as cotton, wool, silk, or combinations thereof. In such examples, the material may have a coating to prevent or limit absorption of fluid into the material, such as a water repellent coating. In some examples, the fluid permeable support 120 may be omitted from the fluid collection device 100. In some examples, the fluid permeable membrane 118 may be optional. For example, the fluid permeable body 115 may include only the fluid permeable support 120.

In some embodiments, the fluid permeable support 120 may have a greater permeability or a greater ability to wick fluids than the fluid permeable membrane 118, such as to move the fluid inwardly from the outer surface of the fluid collection device 100. In some examples, the permeability or the wicking ability of the fluid permeable support 120 and the fluid permeable membrane 118 may be substantially the same.

The fluid permeable membrane 118 and the fluid permeable support 120 may at least substantially completely fill the portions of the interior chamber 104 that are not occupied by the conduit 108. In another example, the fluid permeable membrane 118 and the fluid permeable support 120 may not substantially completely fill the portions of the interior chamber 104 that are not occupied by the conduit 108. In such an example, the fluid collection device 100 includes a reservoir 122 in the interior chamber 104.

The conduit 108 extends into the interior chamber 104. The conduit 108 may be at least partially disposed in the interior chamber 104. The conduit 108 (e.g., a drainage tube) includes an inlet and outlet positioned downstream from the inlet. The conduit 108 may extend into the interior chamber 104 to any point therein. For example, the conduit 108 may be inserted into the interior chamber 104 at a first end region 125 of the fluid collection device 100 and extend therethrough into the first end region 125 or to the second end region 127. The conduit 108 may extend into the fluid impermeable barrier 102 from the first end region 125 through to the reservoir 122 in the second end region 127 such that the inlet of the conduit 108 is in fluid communication with the reservoir 122. The fluid collected in the reservoir 122 may be removed from the interior chamber 104 via the conduit 108.

In some examples, the conduit 108 may enter the interior chamber 104 in the second end region 127 and an inlet of the conduit 108 may be disposed in the second end region 127. The inlet(s) or ports may be a portion of the multiport valve assembly 130. The reservoir 122 may be disposed in the second end region 127 in any of the embodiments disclosed herein. The inlet(s) may be disposed within the fluid permeable support 120 such between the first end region 125 and the second end region 127. Fluids may be removed from the interior chamber 104 via the inlet(s) when suction is applied in the conduit 108.

The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 108 may include silicon or latex. In some examples, the conduit 108 may include one or more portions that are resilient, such as to by having one or more of a diameter or wall thickness that allows the conduit 108 to be flexible. The conduit 108 may be at least partially transparent. In some examples, one or more portions of the conduit 108 may be frosted or opaque (e.g., black) to obscure visibility of the fluid(s) therein.

The fluid impermeable barrier 102, the fluid permeable membrane 118 and the fluid permeable support 120 may be sized and shaped to have the conduit 108 at least partially disposed in the interior chamber 104. For example, at least one of the fluid permeable membrane 118 and the fluid permeable support 120 may be configured to form a space that accommodates the conduit 108. The fluid impermeable barrier 102 may define an aperture sized to receive the conduit 108. The conduit 108 may be disposed in the interior chamber 104 via the aperture. The aperture may be sized and shaped to form an at least substantially fluid tight seal against the conduit 108, thereby substantially preventing the fluid(s) from escaping the interior chamber 104. The fluid collected in the fluid collection device 100 may be removed from the interior chamber 104 via the conduit 108.

The porous material of the fluid permeable body 115 (e.g., fluid permeable membrane 118 and the fluid permeable support 120) may not substantially completely fill the portions of the interior chamber 104 that are not occupied by the conduit 108. In such examples, the fluid collection device 100 includes the reservoir 122 therein. The reservoir 122 is a substantially unoccupied portion of the interior chamber 104. The reservoir 122 may be defined between the fluid impermeable barrier 102 and the porous material of the fluid permeable body 115 (e.g., one or both of the fluid permeable membrane 118 and the fluid permeable support 120). The fluid(s) emitted by the wearer may be wicked into the interior chamber 104 by the porous material of the fluid permeable body 115 and may flow through the fluid permeable membrane 118 and/or fluid permeable support 120 to the reservoir 122. The fluid impermeable barrier 102 may retain the fluid(s) in the reservoir 122. The reservoir 122 may be located in a portion of the fluid collection device expected to be positioned in a gravimetrically low point of the fluid collection device when worn by a person. In such examples, the location of the openings the multiport valve assembly including the conduit 108 and the reservoir 122 at the gravimetrically low point of the fluid collection device allows the fluids collected in the interior chamber 104 to drain into the reservoir 122 when the device is positioned on the wearer. For instance, the fluid(s) in the porous material of the fluid permeable body 115 may flow in any direction due to capillary forces. However, the fluid(s) may exhibit a preference to flow in the direction of gravity, especially when at least a portion of the porous material of the fluid permeable body 115 is saturated with the fluid(s). Accordingly, one or more of the inlet or the reservoir 122 may be located in the second end region 127. While depicted in the second end region 127, a reservoir 122 may be located in any portion of the interior chamber 104 such as the first end region 125 or an intermediate portion therebetween. In such examples, the conduit 108 may extend into the reservoir 122, such as through one or more of the porous material of the fluid permeable body 115 or fluid impermeable barrier 102 in the first end region 125.

Other embodiments of fluid impermeable barriers, fluid permeable membranes, fluid permeable supports, cavities, conduits and their shapes and configurations useful for the fluid collection devices described herein are disclosed in U.S. patent application Ser. No. 15/612,325 filed on Jun. 2, 2017; U.S. patent application Ser. No. 15/260,103 filed on Sep. 8, 2016; and U.S. Pat. No. 10,226,376 filed on Jun. 1, 2017, the disclosure of each of which is incorporated herein, in its entirety, by this reference.

Referring to FIG. 2, the fluid collection device 100 includes the multiport valve assembly 130. The multiport valve assembly 130 includes the conduit 108 and the sheath 132. The sheath 132 is concentrically disposed around the terminal end of the conduit 108 in the interior chamber 104. The sheath 132 and the conduit 108 may be sized and shaped to provide a fit (e.g., interference fit, slip fit, etc.) within each other such that the conduit 108 is movable within the sheath 132 but substantially no fluid flows between the sheath 132 and the conduit 108. The sheath 132 may be constructed of the same or a similar material as the conduit 108. The sheath 132 may have a higher resilience and rigidity than the conduit 108. For example, the sheath 132 may have a rigidity that prevents the sheath 132 and conduit 108 therein from being compressed and occluded when a wearer sits on the device 100. The sheath 132 may be fixed within the fluid collection device 100, such as fixed to one or more of the fluid impermeable barrier 102 or the fluid permeable body 115. For example, the sheath 132 may be adhered to the fluid permeable support or the fluid impermeable barrier 102.

In some embodiments, the multiport valve assembly 130 is rotationally alignable. Sets of the holes in the conduit 108 and sheath 132 align depending upon the rotational position of the sheath 132 with respect to the conduit 108. Such alignment allows fluid to be removed from a medial portion of the interior chamber 104 or the second end region of the interior chamber 104. In some embodiments, to align to form a port or inlet in the interior chamber 104, the sets of holes in the conduit 108 and sheath 132 are longitudinally spaced by the same (first) distance but located on circumferentially different portions as explained below. The terminal end of the conduit 108 (portion of conduit 108 within the interior chamber 104) defines a first plurality of holes thereon. The sheath 132 defines a second plurality of holes therein. The first plurality of holes and the second plurality of holes are spaced to align only one of the first plurality of holes with only one of the second plurality of holes for a selected orientation of the terminal end of the conduit 108 with respect to the sheath 132.

As shown in FIGS. 4-7, various multiport valve assemblies and orientations of the valve assemblies disclosed herein can be used to select a longitudinal location in the valve assembly where a fluid may flow therethrough. Such multiport valve assemblies allow a wearer, healthcare professional, or caregiver to selectively utilize a valve (e.g., port) for removing fluid from a fluid collection device in a gravimetrically low point of the device when the wearer is in a supine position, a standing position, or a sitting position. For example, a port (e.g., valve) in the distal end region (e.g., lower region of the assemblies in FIGS. 4-7) of a multiport valve assembly may be used when a wearer is in a supine position and a port in the medial region (e.g., upper region of the assemblies in FIGS. 4-7) of a multiport valve assembly may be used when a wearer is in a sitting position. As explained in detail below, the ports may be selected by one or more of rotational or longitudinal translation of the conduit with respect to the sheath in the multiport valve assembly.

Figure 4:
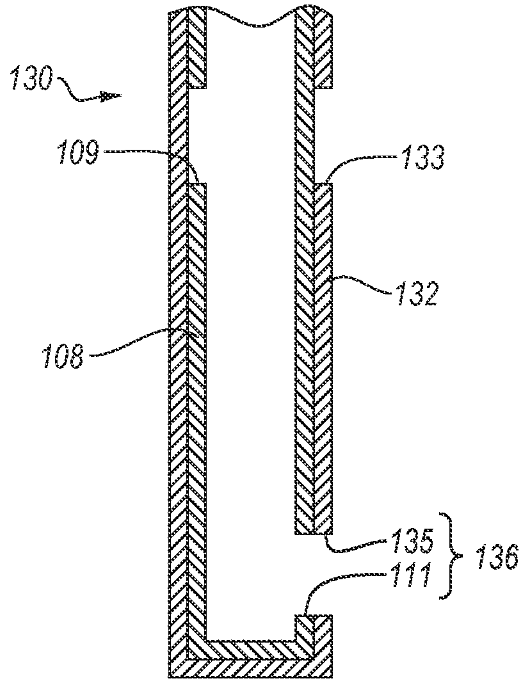
FIG. 4 is a cross-sectional view of the multiport valve assembly of FIGS. 2 and 3 in a first rotational alignment, according to an embodiment.
Figure 5:
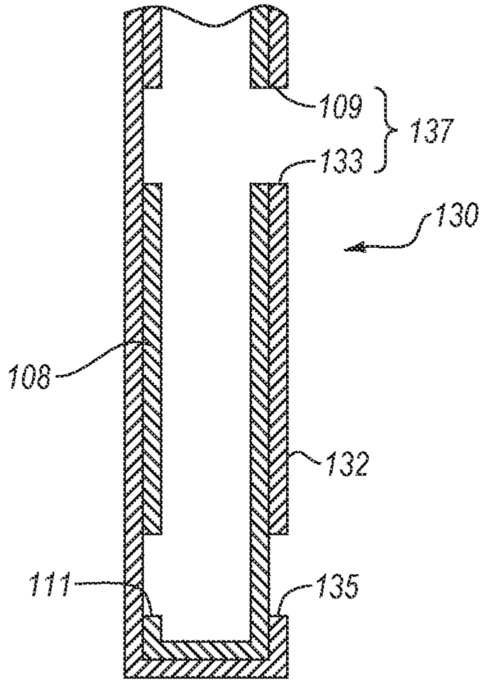
FIG. 5 is a cross-sectional view of the multiport valve assembly of FIGS. 2 and 3 in a second rotational alignment, according to an embodiment.

FIG. 4 is a cross-sectional view of the multiport valve assembly 130 of FIGS. 2 and 3 in a first rotational alignment, according to an embodiment. FIG. 5 is a cross-sectional view of the multiport valve assembly 130 of FIGS. 2 and 3 in a second rotational alignment, according to an embodiment. The first plurality of holes in the conduit 108 includes a conduit distal hole 111 on a first side of the conduit 108 in the second end region 127 and a conduit medial hole 109 on a second side of the conduit 108 and longitudinally spaced from the conduit distal hole 111 by a first distance. The conduit distal hole 111 and the conduit medial hole 109 are on circumferentially opposite sides of the conduit 108. The second plurality of holes in the conduit 108 includes a sheath distal hole 135 on a first side (e.g., facing the opening 106) of the sheath 132 at the second end region 127 and a sheath medial hole 133 on the first side of sheath and longitudinally spaced from the sheath distal hole 135 by the first distance.

As shown in FIGS. 2-4, the conduit 108 is rotatable with respect to the sheath 132. Such rotation allows selective alignment of the medial holes or the distal holes to provide vacuum force in the second end region 127 or the medial region of the interior chamber 104. As shown, the sheath distal hole 135 may be aligned with the conduit distal hole 111 by rotation of the conduit 108 with respect to the sheath 132. However, when the distal holes are aligned in the first rotational alignment shown in FIGS. 3 and 4 to form the distal port 136, the medial holes are out of alignment such that fluids may only be removed via the distal port 136 formed by the aligned distal holes. The second rotational alignment (e.g., 180° rotation with respect to FIGS. 2-4) of FIG. 5 allows the medial holes to align to form the medial port 137 such that the distal holes are out of alignment and fluids may only be removed via the medial port 137 formed by the aligned medial holes.

While two sets of holes (e.g., medial and distal) are disclosed with respect to FIGS. 1-5, in some examples, more than two set of holes may be included in multiport valve systems. In such examples, the sets of holes may be spaced longitudinally and/or circumferentially on the conduit 108 and sheath 132 such that only one set of holes is in alignment at a time.

Figure 6:
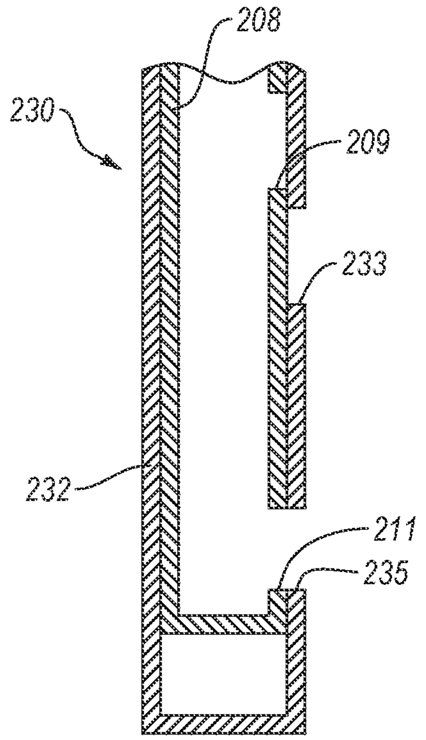
FIG. 6 is a cross-sectional view of a multiport valve assembly in a first longitudinal alignment, according to an embodiment.
Figure 7:
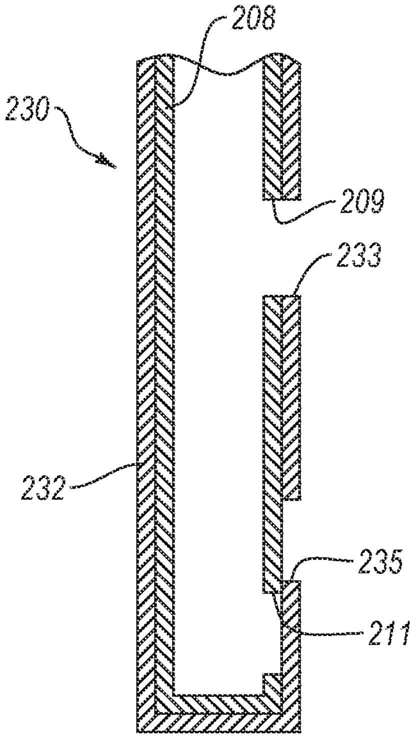
FIG. 7 is a cross-sectional view of the multiport valve assembly in a second longitudinal alignment, according to an embodiment.

Further alignment schemes may be utilized in multiport valve assemblies. For example, a conduit and sheath having a selective longitudinal alignment for the holes thereon may be utilized to control application of vacuum force in the interior chamber of a fluid collection device in specific locations therein. FIG. 6 is a cross-sectional view of the multiport valve assembly 230 in a first longitudinal alignment, according to an embodiment. FIG. 7 is a cross-sectional view of the multiport valve assembly 230 in a second longitudinal alignment, according to an embodiment. The multiport valve assembly 230 may be similar or identical to the multiport valve assembly 130 in one or more aspects. For example, the multiport valve assembly 230 includes the conduit 208 and the sheath 232 concentrically disposed around the conduit 208. The conduit 208 may be similar or identical to the conduit 108 in one or more aspects. The sheath 232 may be similar or identical to the sheath 132 in one or more aspects. The holes on the conduit 208 and the sheath 232 may be rotationally aligned with respect to each other. However, the distance between the holes on the conduit 208 and the distance between the holes on the sheath 232 may differ to allow selective alignment between the medial and distal holes by longitudinal movement of the conduit 208 with respect to the sheath 232.

The multiport valve assembly 230 includes a terminal end of the conduit 208, the terminal end of the conduit 208 defining a first plurality of holes thereon. The multiport valve assembly 130 include the sheath concentrically disposed over the terminal end of the conduit 108 within the interior chamber, the sheath defining a second plurality of holes therein. The first plurality of holes and the second plurality of holes are spaced to align only one of the first plurality of holes with only one of the second plurality of holes for a selected orientation of the terminal end of the conduit 208 with respect to the sheath 232. The first plurality of holes include a conduit distal hole 211 on a first side of the conduit 208 at a second end region of a fluid collection device and a conduit medial hole 209 on the first side of the conduit 208 and longitudinally spaced from the conduit distal hole 211 by a first distance. The second plurality of holes include a sheath distal hole 235 on a first side of the sheath 232 at a second end region of the fluid collection device and a sheath medial hole 233 on the first side of sheath 232 and longitudinally spaced from the sheath distal hole 235 by a second distance that is different than the first distance. The conduit 208 is longitudinally movable within and with respect to the sheath 232. The difference of the first distance and the second distance may be greater than the diameter of the holes in the conduit 208 and sheath 232. Accordingly, when the conduit 208 is moved longitudinally in the sheath 232, the distal holes or the medial holes may align and the other of the distal holes or the medial holes may not overlap such that vacuum applied through conduit 208 is only applied to the interior chamber of the fluid collection device through one set of holes.

As shown in FIG. 6, the first longitudinal relationship of the conduit 208 to the sheath 232 may be without the conduit 208 disposed in the distal extent of the sheath 232. In such examples, the distal holes may be aligned to form a port in the distal end of the multiport valve assembly 230 and fluid collection device including the same. As shown in FIG. 7, the second longitudinal relationship of the conduit 208 to the sheath 232 may be with the conduit 208 disposed in the distal extent of the sheath 232. In such examples, the medial holes may be aligned to form a port in a medial portion of the multiport valve assembly 230 and fluid collection device including the same.

Figure 8:
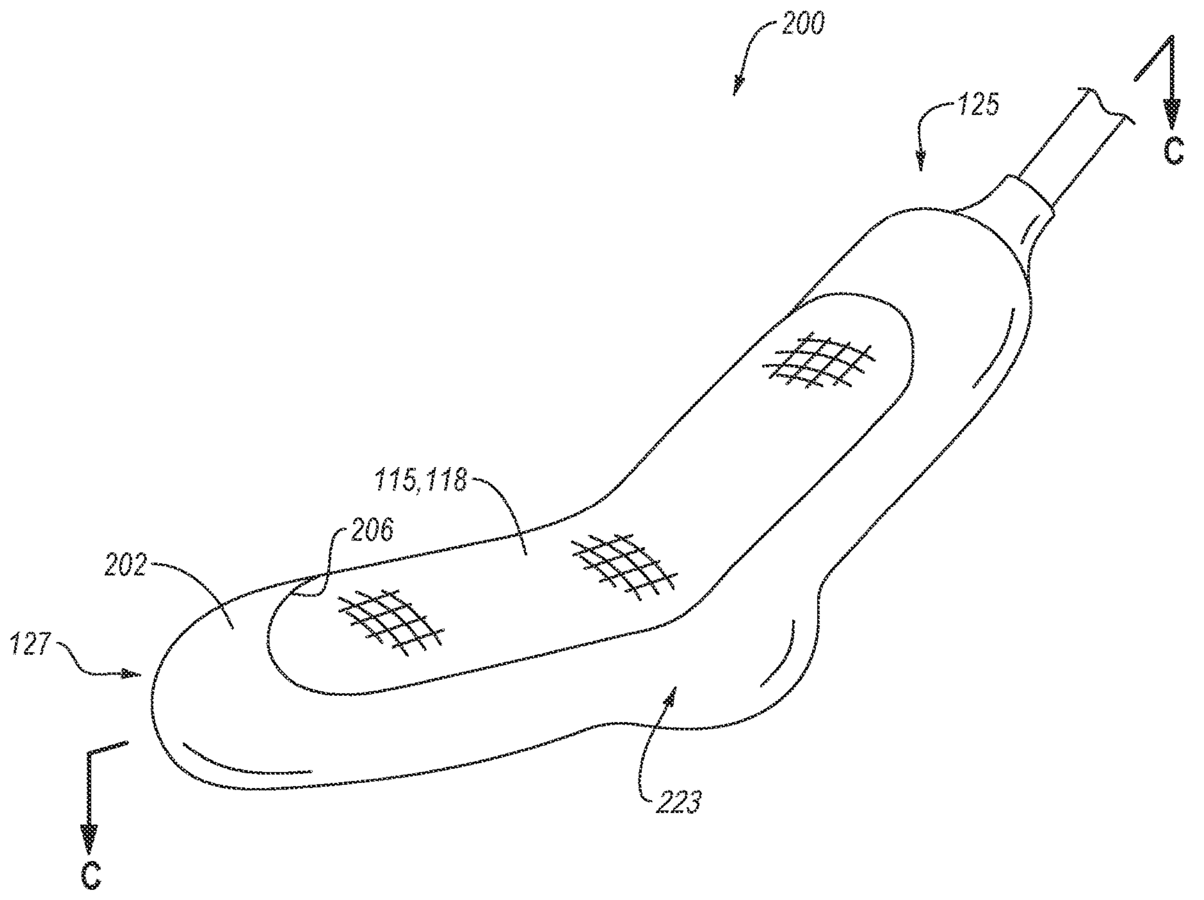
FIG. 8 is an isometric view of a fluid collection device, according to an embodiment.
Figure 9:
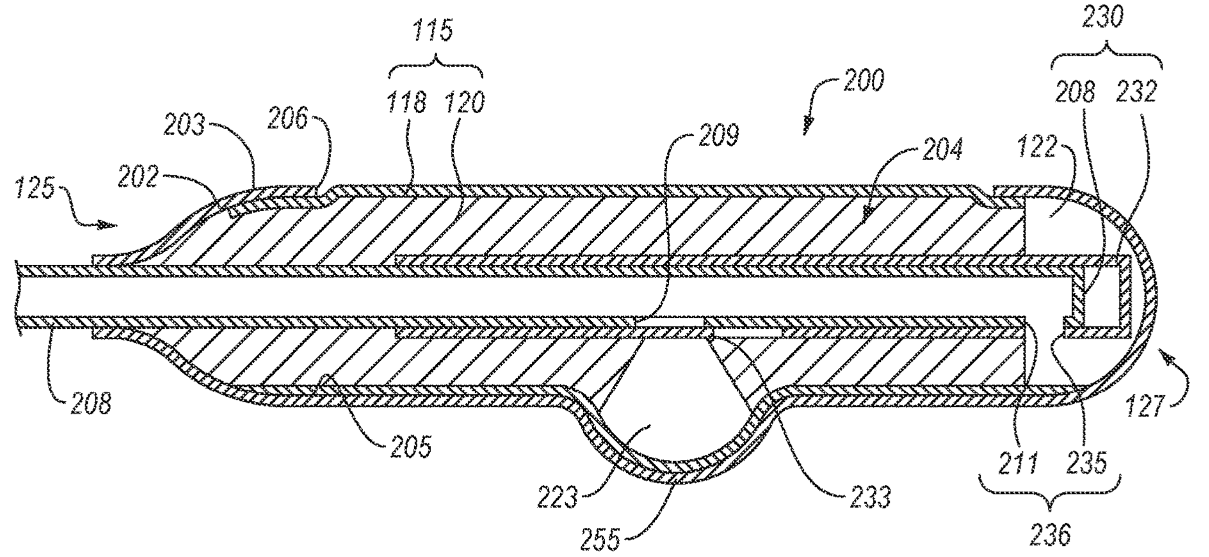
FIG. 9 is a cross-sectional view of the fluid collection device of FIG. 8 taken along the plane C-C, according to an embodiment.

FIG. 8 is an isometric view of a fluid collection device 200, according to an embodiment. FIG. 9 is a cross-sectional view of the fluid collection device 200 of FIG. 8 taken along the plane C-C, according to an embodiment. The fluid collection device 200 is sized, shaped, and composed to collect urine from the urethra of a wearer. The fluid collection device 100 includes a fluid impermeable barrier 202 defining an interior chamber 204 therein, a fluid permeable body 115 disposed in the interior chamber 204, the conduit 208 disposed in the interior chamber 204, the multiport valve assembly 230 of FIGS. 6 and 7 disposed within the interior chamber 204. The multiport valve assembly 230 to allows a user to select a port (e.g., valve) from a plurality of ports through which the urine is remove via the conduit 208. The fluid permeable body 115 may be exposed to the external environment via the opening 106 in the fluid impermeable barrier 202. During use, the fluid collection device 200 may be positioned over the urethra of the wearer and urine may be received into the fluid collection device 200 by the fluid permeable body 115 via the opening 206. The urine may be removed from the fluid collection device 200 via the conduit 208 disposed within the interior chamber 204 via one of the ports in the multiport valve assembly 230.

The fluid impermeable barrier 202 is similar or identical to the fluid impermeable barrier 102 in one or more aspects. The fluid impermeable barrier 202 at least partially defines the interior chamber 204 and opening 106. For example, the inner surface(s) 205 of the fluid impermeable barrier 202 at least partially defines the interior chamber 204 within the fluid collection device 200. The fluid impermeable barrier 202 at least temporarily retains the fluid(s) in the interior chamber 204. The fluid impermeable barrier 202 may include a bulbous portion 255 in the medial region between the first end region 125 and the second end region 127. The bulbous portion 255 may form at least a portion of a reservoir 223 in the medial region of the interior chamber 204.

The fluid permeable body 115 may fill at least some of the interior chamber 204. The fluid permeable body 115 may not fill all of the unoccupied portions of the interior chamber 204. In such examples, the fluid collection device 200 includes one or more reservoirs 122 or 223 therein. The reservoir 122 may be located in the second end region 127 as disclosed above with respect to the fluid collection device 100. Such a reservoir is useful when the second end region is located at a gravimetrically low point of the fluid collection device 200 such as when the wearer is in a supine, laying, or reclining position.

The reservoir 223 may be located in the medial region of the of interior chamber 204, such as substantially opposite the opening 106. The reservoir 223 may be located between the sheath 232 and fluid impermeable barrier 202 opposite the opening 106. The reservoir 223 may not include one or more of the fluid permeable membrane 118 or the fluid permeable support 120 therein. In some examples (not shown), the reservoir 223 may include an empty space between a substantially cylindrical fluid permeable body 115 and the bulbous portion 255. Such examples with reservoirs located in the medial portion may be particularly useful when a wearer is in a sitting position, such as when the fluid collection device is bent and the medial portion is at a gravimetrically low point of the device.

In some examples (not shown), no reservoir 223 may be included. In such examples, the bulbous portion 255 may allow fluids to gather in the medial region such that use of a medial port to remove the same would be desirable. For example, the fluid permeable body may fill at least some of the space depicted as the reservoir 223 in FIG. 9.

The fluid collection device 200 includes the multiport valve assembly 230 disclosed above. The multiport valve assembly 230 may be used to select a medial port in the medial region (e.g., aligned medial holes 209 and 233) or the distal port 236 (e.g., aligned distal holes 211 and 235) as shown. For example, the conduit 208 may be moved toward the second end region 127 with respect to the sheath 232 to align the conduit medial hole 209 with the sheath medial hole 233 to form a medial port (not shown). The sheath 232 may be fixed relative to the fluid permeable body 215 and fluid impermeable barrier 202. Accordingly, the conduit 208 may move within the sheath 232 to align the holes thereon.

In some examples, the fluid collection devices disclosed herein may include an alignment assembly to align the conduit with the sheath to ensure alignment of the holes thereon to provide egress for fluids collected in the device. Various alignment assemblies may be utilized with a multiport valve assembly.

Figure 10:
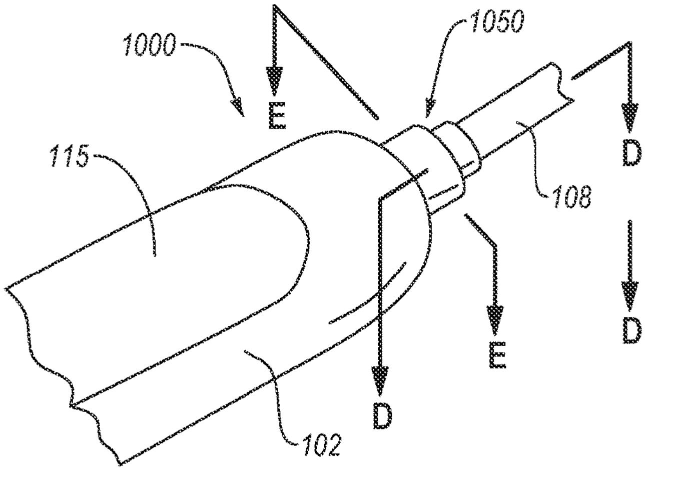
FIG. 10 is a partial isometric view of a fluid collection device, according to an embodiment.
Figure 11:
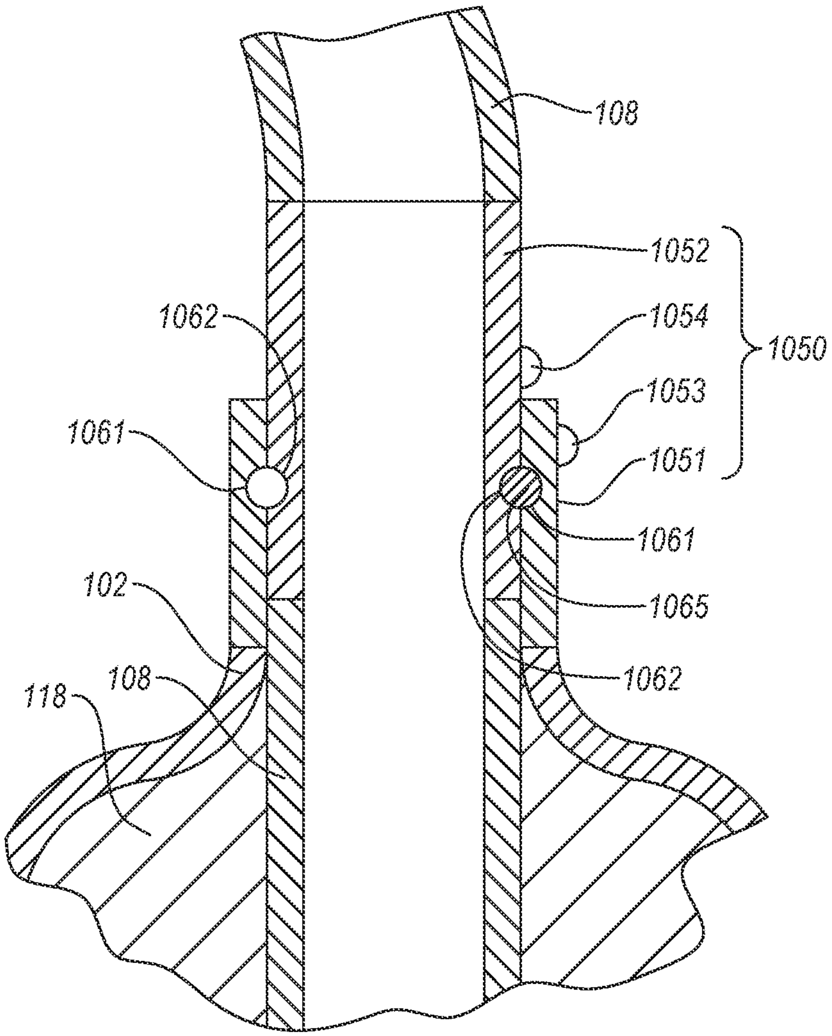
FIG. 11 is a cross-sectional view of the fluid collection device of FIG. 10 taken along the plane D-D, according to an embodiment.
Figure 12:
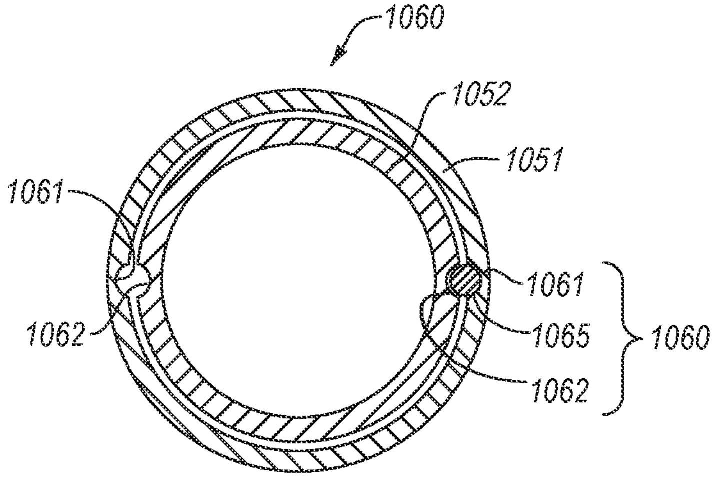
FIG. 12 is a cross-sectional view of the fluid collection device of FIG. 10 taken along the plane E-E, according to an embodiment.

FIG. 10 is a partial isometric view of a fluid collection device 1000, according to an embodiment. FIG. 11 is a cross-sectional view of the fluid collection device 1000 of FIG. 10 taken along the plane D-D, according to an embodiment. FIG. 12 is a cross-sectional view of the fluid collection device 1000 of FIG. 10 taken along the plane E-E, according to an embodiment. The fluid collection device 1000 is similar or identical to the fluid collection device 100 in one or more aspects. For example, the fluid collection device 1000 may include a fluid impermeable barrier 102, a fluid permeable body 115, a conduit 108, and a multiport valve assembly as disclosed herein. The fluid collection device 1000 includes an alignment assembly 1050.

The alignment assembly 1050 may be connected to the fluid impermeable barrier 102 and the conduit 108. For example, the alignment assembly 1050 may be disposed around the conduit 108 on the first end of the fluid impermeable barrier. The alignment assembly 1050 may include a fixed collar 1051 and an inner collar 1052 disposed within the fixed collar 1051. The fixed collar 1051 and the inner collar 1052 may be formed of an at least semi-rigid material such as a polymer, metal, or the like. Suitable polymers may include any of the polymers disclosed herein for the fluid impermeable barrier 102 or the conduit 108. For example, suitable polymers may include one or more of polyether ether ketone ("PEEK"), polypropylene, polyethylene, polyethylene terephthalate, thermoplastic elastomer(s), a polycarbonate, or the like.

The fixed collar 1051 may be operably coupled to the fluid impermeable barrier 102 such as via adhesive, welding, crimp, tension fit, or the like. The inner collar 1052 may be operably coupled to the terminal end of the conduit 108, the inner collar 1052 being disposed within the fixed collar 1051. Accordingly, rotation of the inner collar 1052 with respect to the fixed collar 1051 rotates the conduit with respect to the sheath (and the rest of the fluid collection device 1000). The fixed collar 1051 and the inner collar 1052 may have markings to align the conduit distal hole with the sheath distal hole and the conduit medial hole with the sheath medial hole. The markings on the fixed collar 1051 may correspond to the position of the sheath distal hole and the sheath medial hole on the sheath and the markings on the inner collar 1052 may correspond to the location of the conduit distal hole and the conduit medial hole on the conduit. For example, the fixed collar 1051 may have a first marking 1053 indicating the circumferential position of the holes on the sheath and the inner collar 1052 may have at least a second marking 1054 indicating the circumferential position of the conduit distal hole and the conduit medial hole. When aligned circumferentially, the first marking 1053 and the at least a second marking 1054 indicate that the sheath holes are in circumferential alignment with one of the conduit distal hole and the conduit medial hole. A 180° rotation would align the other of the conduit distal hole and the conduit medial hole.

The alignment assembly 1050 may include a locking mechanism 1060 to at least temporarily retain position of the inner collar 1052 relative to the fixed collar 1051. Locking mechanism 1060 may include one or more notches 1061 facing inward on the fixed collar 1051 and one or more notches 1062 facing outward on the inner collar 1052. The one or more notches 1061 and 1062 may be in alignment with the holes in the conduit and the sheath. For example, a first notch 1061 on the inner collar 1052 may circumferentially align with the conduit distal hole and the second notch 1062 on the inner collar 1052 (e.g., 180° from the first notch) may circumferentially align with the conduit medial hole. One of the notches 1061 on the fixed collar 1051 may circumferentially align with the sheath distal hole and the sheath medial hole. The one or more notches 1061 and 1062 may be in longitudinal alignment such that when the inner collar 1052 is rotated with respect to the fixed collar 1051, the notches 1061 and 1062 may align circumferentially. The respective notches may be aligned with the respective markings to indicate what position the multiport valve assembly is currently holding.

The locking mechanism 1060 may include a pin, ball, a spring, or any other means of holding notches in place with respect to each other. For example and as shown in FIG. 12, the locking mechanism 1060 may include a ball 1065 disposed in the notch of one of the fixed collar 1051 or the inner collar 1052. The ball 1065 may be permanently retained within one notch, such as the notch 1061 of the fixed collar 1051 as shown. When rotated, the notches 1062 on the inner collar 1052 may at least partially accommodate the ball 1065 to at least temporarily "lock" the inner collar 1052 with respect to the fixed collar 1051. Accordingly, the ball 1065 holds the collars in place when the notches 1061 and 1062 are circumferentially aligned.

In some examples, the locking mechanism 1060 may include a spring loaded locking mechanism, such as having a spring loaded pin, ball, or other structure which is positioned, sized, and shaped to automatically bias into a notch to retain the inner collar 1052 relative to the fixed collar 1051. As noted herein, the locking mechanism 1060 can be positioned to lock into position when the markings on the inner collar 1052 are aligned with the markings on the fixed collar 1051.

The alignment assembly 1050 and the locking mechanism 1060 may be used with the circumferentially alignable multiport valve assembly 30 of FIGS. 1-5.

Figure 13:
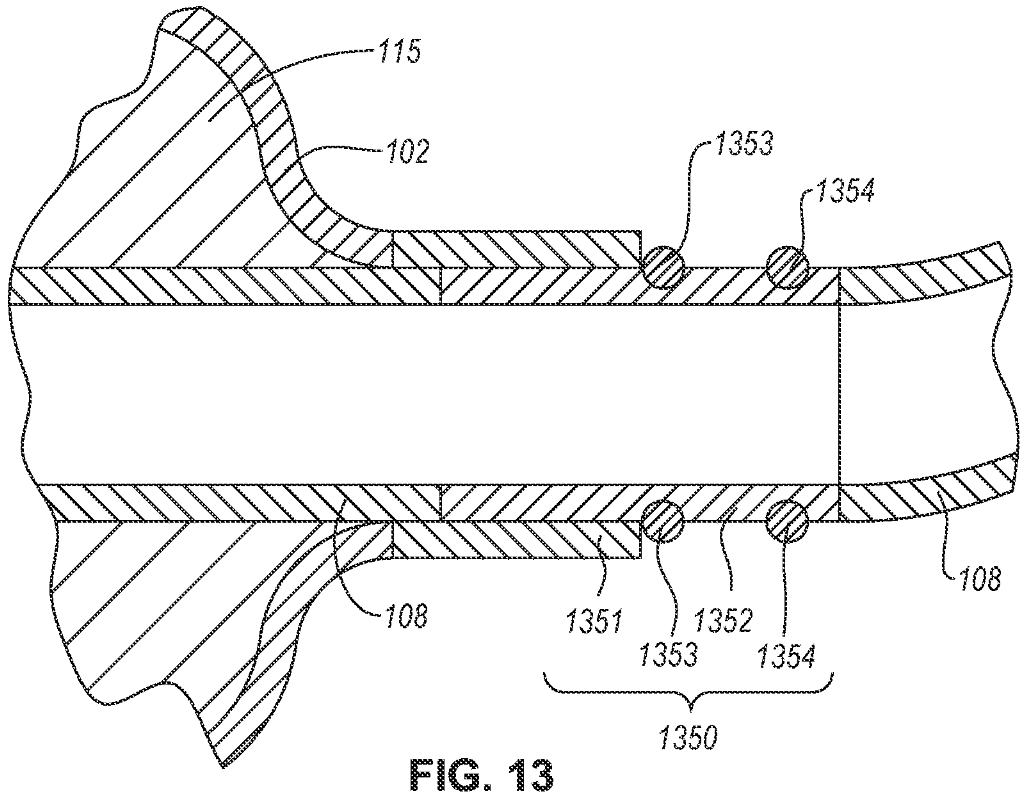
FIG. 13 is a cross-sectional view of an alignment assembly in a first positional relationship, according to an embodiment.
Figure 14:
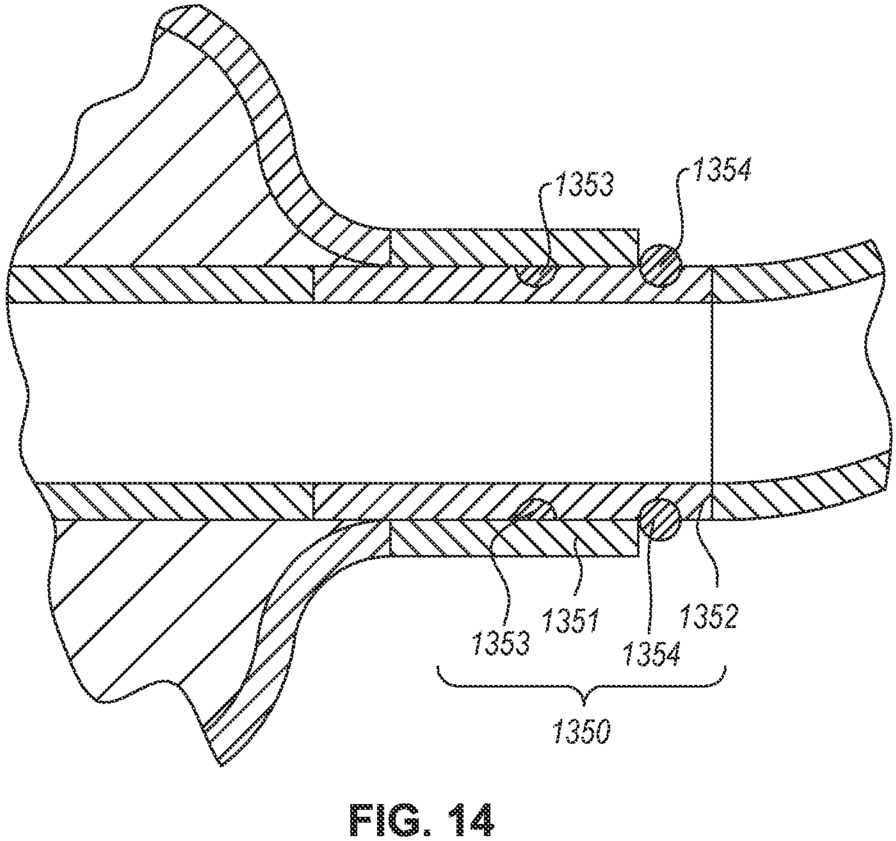
FIG. 14 is a cross-sectional view of the alignment assembly in a second positional relationship, according to an embodiment.

Alignment assemblies useful for the multiport valve assemblies disclosed herein may include longitudinal alignment assemblies. For example, an alignment assembly may provide an indication of, or retain the conduit relative to the sheath to when sets of holes thereon are aligned. FIG. 13 is a cross-sectional view of an alignment assembly 1350 in a first positional relationship, according to an embodiment. FIG. 14 is a cross-sectional view of the alignment assembly 1350 in a second positional relationship, according to an embodiment. The alignment assembly 1350 is disposed around the conduit 108 on a first end of the fluid impermeable barrier 102. The alignment assembly 1350 includes a fixed collar 1351 and an inner collar 1352. The fixed collar 1351 and the inner collar 1352 are similar or identical to the fixed collar 1051 and the inner collar 1352 in one or more aspects. The fixed collar 1351 is operably coupled to the fluid impermeable barrier 102 and the inner collar 1352 is operably coupled to the terminal end of the conduit 108, the inner collar 1352 being disposed within the fixed collar 1351.

The inner collar 1352 is longitudinally movable with respect to the fixed collar 1351. The conduit medial hole and the conduit distal holes on the conduit are spaced from each other by a first distance and the sheath medial hole and medial distal hole on the sheath are spaced by a second distance that is different than the first distance. The inner collar 1352 is longitudinally movable in the fixed collar 1351 by the difference between the first distance and the second distance. The difference between the first distance and the second distance may be larger than the diameter of the holes in the sheath and conduit. Accordingly, when the holes (e.g., distal or medial) that are not aligned do not overlap and are therefore sealed when the other holes (e.g., medial or distal) are aligned.

One or more of the fixed collar 1351 and the inner collar 1352 may have markings 1353 or 1354 thereon to align the conduit distal hole with the sheath distal hole and the conduit medial hole with the sheath medial hole of the multiport valve assembly of a fluid collection device including the alignment assembly 1350. The markings on the inner collar 1352 may correspond to the location of the conduit distal hole and the conduit medial hole on the conduit of a multiport valve assembly connected thereto. As shown, the marking 1353 may indicate the position of the conduit medial hole and the marking 1354 may indicate the position of the conduit distal hole. As shown in FIG. 13, alignment of the marking 1353 with a longitudinal end of the fixed collar 1351 may indicate that the conduit medial hole is in alignment with the sheath medial hole. As shown in FIG. 14, alignment of the marking 1354 with a longitudinal end of the fixed collar 1351 may indicate that the conduit distal hole is in alignment with the sheath medial hole.

The alignment assembly 1350 may include a locking mechanism to at least temporarily retain the position of the inner collar 1352 and conduit relative to the fixed collar 1351 and the sheath. The locking mechanism for the alignment assembly 1350 may be similar or identical to the locking mechanism 1060 (FIGS. 11 and 12) in one or more aspects. For example, the locking mechanism may include notches in one or more of the fixed collar 1351 or the inner collar 1352 along with a pin, a ball, a spring, or any other means of holding notches in place with respect to each other. For example, the fixed collar 1351 may include a notch and the inner collar 1352 may include balls, pins, or the like extending outwardly therefrom and longitudinally spaced in positions thereon to align the medial holes or the distal holes on the conduit and sheath, respectively. When the notch aligns with a first ball, the first ball may fall into the notch and at least temporarily retain the inner collar 1352 with respect to the fixed collar 1351. The first ball may correspond to the alignment of the distal holes or medial holes on the conduit and sheath of the alignment assembly 1050 (FIGS. 11 and 12). A second ball may correspond to the alignment of the other of the distal holes or medial holes on the conduit and sheath of the alignment assembly 1050.

The alignment assembly 1350 may include a spring loaded locking mechanism configured to retain the inner collar 1352 relative to the fixed collar 1351 when the sheath distal hole is aligned with the conduit distal hole, the sheath medial hole is aligned with the conduit medial hole, or when the markings on the fixed collar and/or inner collar indicate one of the foregoing. For example, the ball, a pin, or the like may be spring loaded to be biased into a notch when the inner collar 1352 is move longitudinally with respect to the fixed collar 1351.

The alignment assembly 1350 and the locking mechanism may be used with the longitudinally alignable multiport valve assembly 230 of FIGS. 6-9.

The port in a medial portion of a fluid collection device may be more useful than a port in the second end region of the fluid collection device or vice versa when the wearer is in a specific position. For example, the gravimetrically low point of the fluid collection device may change depending upon the positioning of the wearer.

Figure 15:
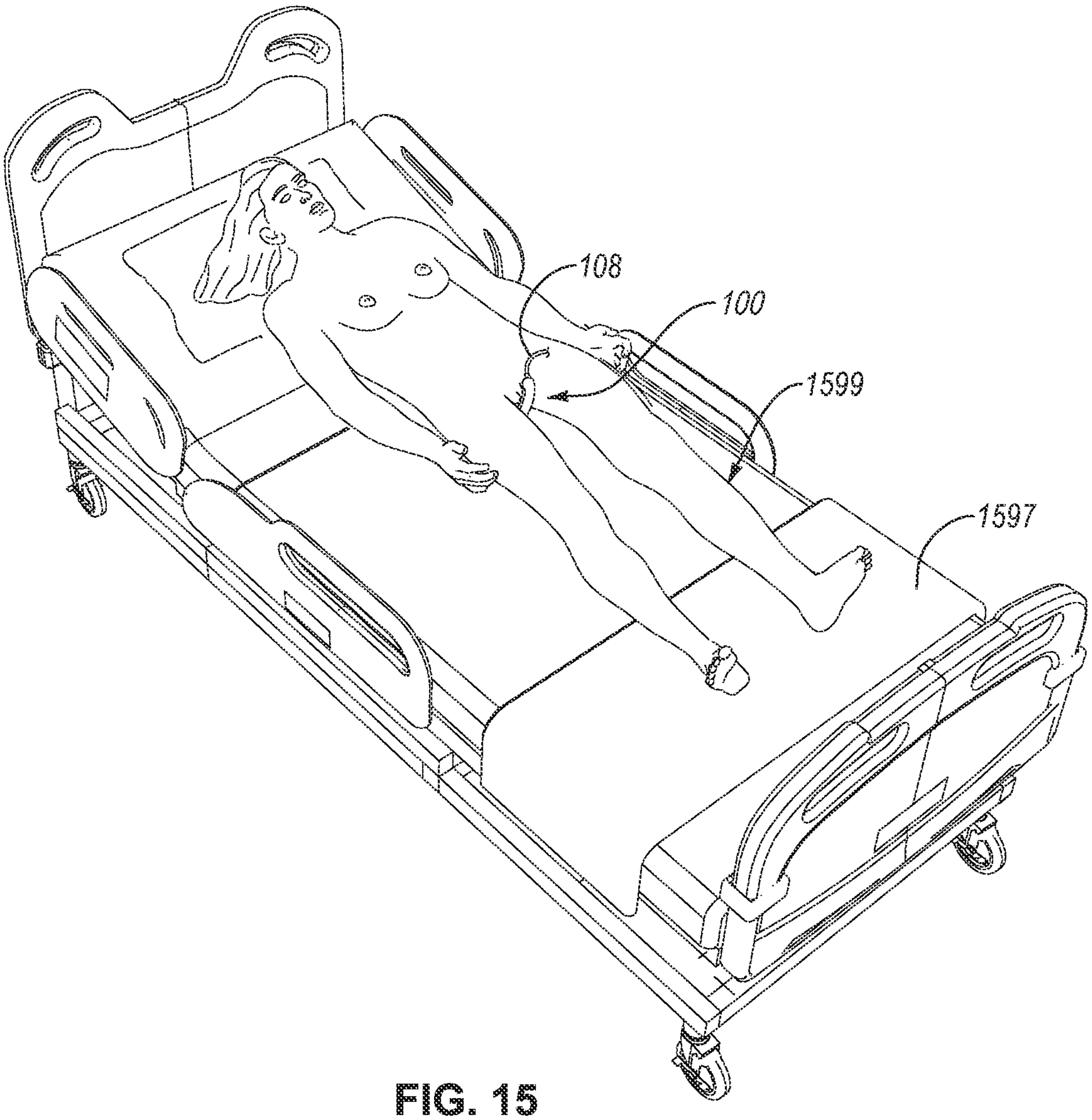
FIG. 15 is an isometric view of a wearer using a fluid collection device in a supine position, according to an embodiment.

FIG. 15 is an isometric view of a wearer 1599 using a fluid collection device 100 in a supine position, according to an embodiment. As shown, the fluid collection device 100 may be positioned between the legs of the wearer 1599 with the second end region facing downward to make the gravimetrically low point the second end region. Such a configuration may be present when the wearer is supine, reclined, or the like, such as when in a bed 1597. In such a configuration, the distal holes in the alignment assembly therein may be selectively aligned to facilitate draining from the second end region.

Figure 16:
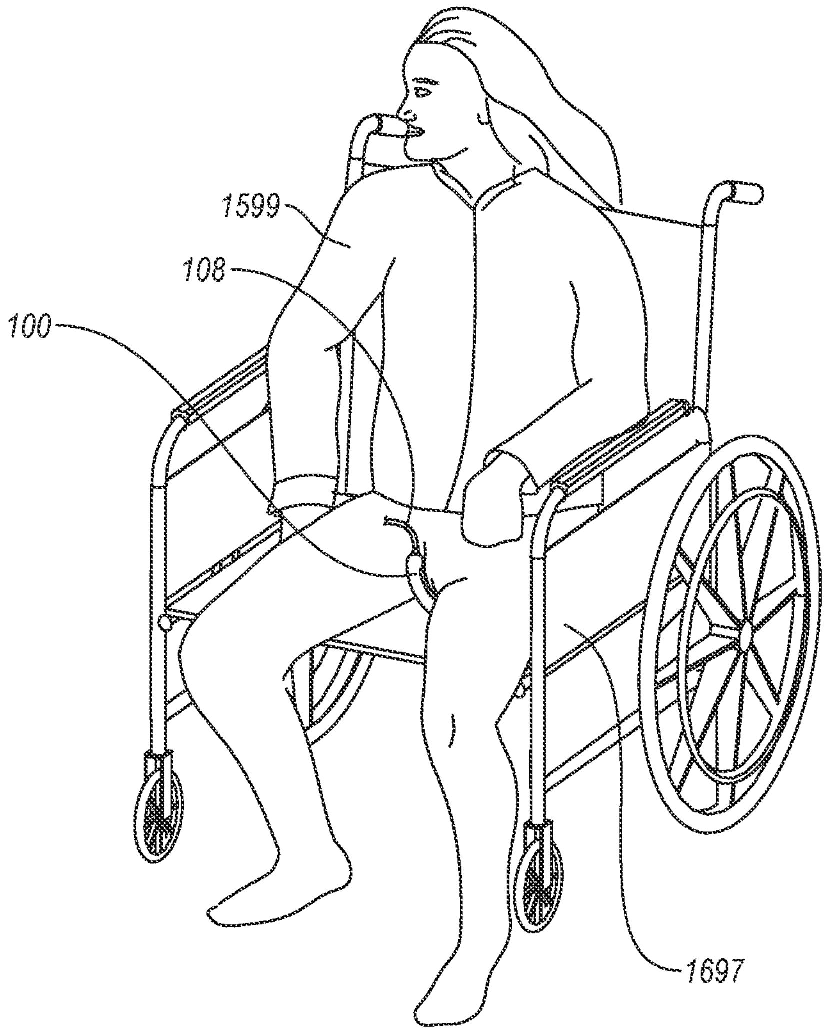
FIG. 16 is an isometric view of a wearer using a fluid collection device in a sitting position, according to an embodiment.

FIG. 16 is an isometric view of a wearer 1599 using a fluid collection device 100 in a sitting position, according to an embodiment. As shown, the fluid collection device 100 may be positioned between the legs of the wearer 1599 with the medial region facing downward to make the gravimetrically low point the medial region. Such a configuration may be present when the wearer is sitting and the fluid collection device is bent, bowed, or curved, such as when the wearer is sitting in a wheelchair 1697, a chair, or a car seat. In such a configuration, the medial holes in the alignment assembly therein may be selectively aligned to facilitate draining from the medial region.

Any of the fluid collection devices disclosed herein may be used in FIGS. 15-16. For example, the fluid collection device 200 with the bulbous portion 255 may be particularly useful when the wearer is expected to be sitting.

Figure 17:
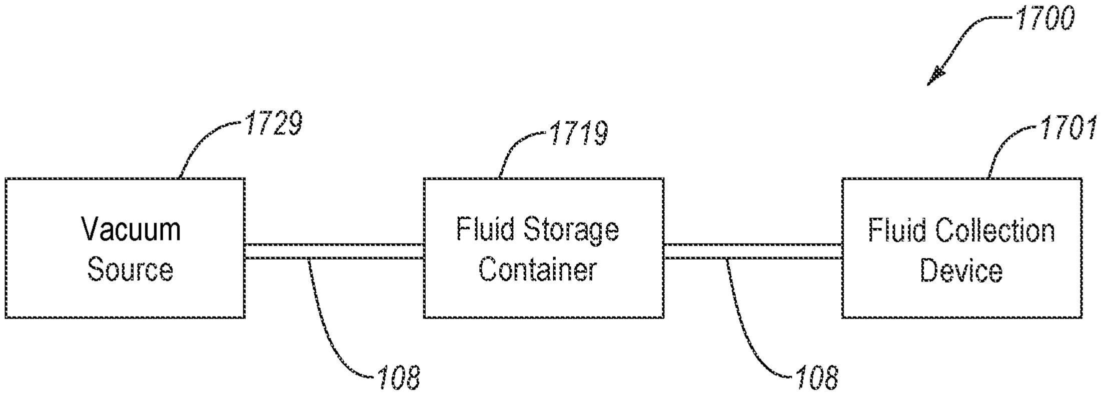
FIG. 17 is a block diagram of a system for collecting fluid, according to an embodiment.

Any of the fluid collection devices disclosed herein may be used in systems for collecting fluids such as urine and vaginal discharge from a wearer. FIG. 17 is a block diagram of a system 1700 for collecting fluid, according to an embodiment. The system 1700 includes a fluid collection device 1701, a fluid storage container 1719, and a vacuum source 1729. The fluid collection device 1701, the fluid storage container 1719, and the vacuum source 1729 may be fluidly coupled to each other via one or more conduits 108. For example, fluid collection device 1701 may be operably coupled (e.g., fluidly connected) to one or more of the fluid storage container 1719 or the vacuum source 1729 via the conduits 108.

The fluid collection device 1701 may be similar or identical to any of the fluid collection devices disclosed herein. For example, the fluid collection device 1701 may include a fluid impermeable barrier, a fluid permeable body, and an alignment assembly as disclosed herein. The fluid collection device may include any of the alignment assemblies disclosed herein. The fluid collection device 1701 may include the conduit 108 including at least one inlet (e.g., distal and medial holes) and an outlet as disclosed herein. The outlet may be fluidly coupled to the fluid storage container 1719 and the inlet(s) may be positioned in the fluid collection device 1701 such as in a portion of the interior chamber therein selected to be at a gravimetrically low point of the fluid collection device 1701 when worn by a user (e.g., reservoir(s)).

The conduit 108 is coupled to and at least partially extends between one or more of the fluid storage container 1719 and the vacuum source 1729. Accordingly, the vacuum source 1729 may be fluidly connected to the fluid storage container 1719 via the conduit 108. In an example, the conduit 108 is directly connected to the vacuum source 1729. In some examples, the conduit 108 may be indirectly connected to at least one of the fluid storage container 1719 and the vacuum source 1729. In some examples, the conduit 108 may be secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

Fluid (e.g., urine or other bodily fluids) collected in the fluid collection device 1701 may be removed from the fluid collection device 1701 via the conduit 108. Vacuum or suction force may be applied to remove fluid from the fluid collection device via the conduit either directly or indirectly. The vacuum force may be applied indirectly via the fluid storage container 1719. For example, the second open end of the conduit 108 may be disposed within the fluid storage container 1719 and an additional conduit 108 may extend from the fluid storage container 1719 to the vacuum source 1729. Accordingly, the vacuum source 1729 may indirectly apply vacuum or suction force into the fluid collection device 1701 (e.g., chamber therein) via the fluid storage container 1719 and conduit 108. As the fluid is drained from the interior chamber of the fluid collection device 1701, the fluid may travel through the first section of conduit 108 to the fluid storage container 1719 where it may be retained. The fluid storage container 1719 is constructed to store fluids therein. The fluid storage container 1719 may be a substantially rigid container, such as a jar, a canister, or the like. The fluid storage container may include a bag in some examples.

The vacuum source 1729 may include one or more of a vacuum pump, a wall-mounted vacuum line, or a hand pump. For example, the vacuum source 1729 may include one or more of a manual vacuum pump, and electric vacuum pump, a diaphragm pump, a centrifugal pump, a displacement pump, a magnetically driven pump, a peristaltic pump, or any pump configured to produce a vacuum. In examples, the vacuum source 1729 may be a portable vacuum source powered by one or more of a power cord (e.g., connected to a power socket), one or more batteries, or even manual power (e.g., a hand operated vacuum pump).

Any of the fluid collection devices or systems disclosed herein may be utilized to collect one or more fluids from a wearer of the fluid collection device.

Figure 18:
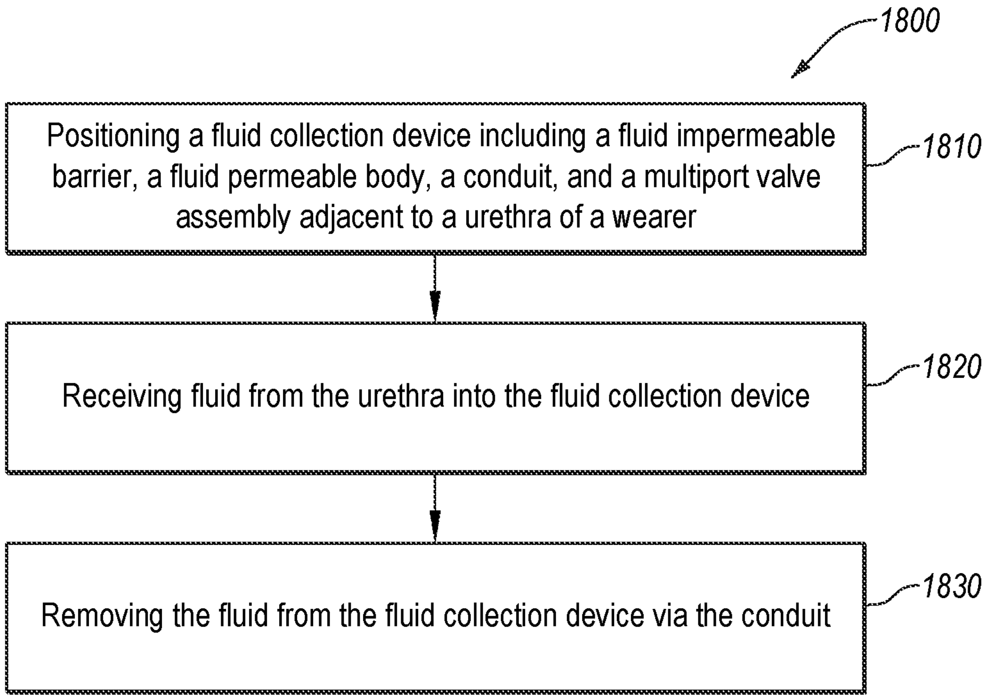
FIG. 18 is a flow diagram of a method for collecting fluid, according to an embodiment.

FIG. 18 is a flow diagram of a method 1800 for collecting fluid, according to an embodiment. The method 1800 includes a block 1810 of positioning any of the fluid collection devices disclosed herein adjacent to a urethra of a wearer; a block 1820 of receiving fluid from the urethra into the fluid collection device; and a block 1830 of removing the fluid from the fluid collection device via the conduit. Any the blocks 1810, 1820, or 1830 of the method 1800 may be performed in different orders, split into multiple acts, modified, supplemented, or combined. For example, the blocks 1820 and 1830 may be combined into a single block. In some examples, one or more of the blocks 1810-1830 of the method 1800 may be omitted.

Block 1810 of positioning any of the fluid collection devices disclosed herein adjacent to a urethra of a wearer may include utilizing any of the fluid collection devices disclosed herein. For example, the fluid collection device 1701 includes any of the alignment assemblies disclosed herein. Positioning any of the fluid collection devices disclosed herein adjacent to a urethra of a wearer may include positioning the opening on, around or over the labia or vulva of the wearer. Positioning any of the fluid collection devices disclosed herein adjacent to a urethra of a wearer may include positioning the second end region of the fluid collection device against or near the perineal region of the wearer with the first end region against or near the pubic region of the wearer.

Positioning any of the fluid collection devices disclosed herein adjacent to a urethra of a wearer may include positioning the opening of the fluid collection device over, on, or in contact with the urethra of the wearer. Positioning any of the fluid collection devices disclosed herein adjacent to a urethra of a wearer may include positioning the fluid collection device on the wearer effective to locate a medial port or a distal port of the multiport valve assembly at a gravimetrically low point of the fluid collection device.

Block 1820 of receiving fluid from the urethra into the fluid collection device may include receiving the fluid into fluid permeable body, such as via the opening. Receiving fluid from the urethra into the fluid collection device may include wicking or otherwise allowing the fluid to flow into the interior chamber of the fluid collection device via the fluid permeably body (e.g., fluid permeable membrane and fluid permeable support). Receiving fluid from the urethra into the fluid collection device may include may include flowing the fluid towards a portion of the interior chamber of the fluid collection device that is fluidly coupled to one or more of a gravimetrically low portion of the fluid chamber, a port (e.g., an inlet) of a conduit or multiport valve assembly, or a reservoir.

Block 1830 of removing the fluid from the fluid collection device via the conduit may include removing at least some of the fluid from the interior chamber of the fluid collection device. Removing the fluid from the fluid collection device via the conduit may include removing at least some of the fluid from the fluid permeable body of the fluid collection device. Removing the fluid from the fluid collection device via the conduit may include applying a vacuum in the interior chamber, such as via any of the vacuum sources disclosed herein. In such examples, the removing may include activating the vacuum source. Removing the fluid from the fluid collection device via the conduit may include removing the fluid into a fluid storage container.

The method 1800 may include selecting a port (e.g., inlet or valve) of the multiport valve assembly. Selecting a port of the multiport valve assembly rotating the conduit with respect to or relative to the sheath, such as rotating the conduit inside of the sheath to align a conduit distal hole with a sheath distal hole or a conduit medial hole with a sheath medial hole. Selecting a port of the multiport valve assembly may include moving the conduit longitudinally with respect to the sheath, such as moving the conduit inside of the sheath to align a conduit distal hole with a sheath distal hole or a conduit medial hole with a sheath medial hole.

Selecting a port of the multiport valve assembly may include aligning markings on an alignment assembly, which causes the conduit to move with respect to the sheath either rotationally or longitudinally. Selecting a port of the multiport valve assembly may include aligning a locking mechanism on the alignment assembly, which causes the conduit to move with respect to the sheath either rotationally or longitudinally, effective to lock the alignment assembly and the conduit with respect to the sheath when the distal holes or the medial holes are aligned.

Selecting a port of the multiport valve assembly may be carried out prior to, contemporaneously with, or after positioning any of the fluid collection devices disclosed herein adjacent to a urethra of a wearer.

The method 1800 may include collecting the fluid(s) that are removed from the fluid collection device, such as in the fluid storage container. The method may include one or more of testing or quantifying the amount of fluid removed.

The fluid collection devices, systems, and methods disclosed herein provide for secure attachment of fluid collection devices to collect fluids emitted from a wearer, which prevents leakage and soiling of the wearer's clothing, bedding, and care takers.

As used herein, the term "about" or "substantially" refers to an allowable variance of the term modified by "about" by ±10% or ±5%. Further, the terms "less than," "or less," "greater than", "more than," or "or more" include as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A fluid collection device, comprising:

a fluid impermeable barrier at least partially defining an interior chamber and an opening through which the interior chamber is exposed to an external environment;

a fluid permeable body positioned at least partially within the interior chamber to extend across at least a portion of the opening and configured to wick fluid away from the opening;

a conduit extending into the interior chamber, the conduit defining a first plurality of holes on a side wall thereof, the first plurality of holes including a first conduit hole and a second conduit hole; and a multiport valve assembly disposed within the interior chamber, the multiport valve assembly including a sheath concentrically disposed over at least a portion of the conduit within the interior chamber, the sheath defining a second plurality of holes on a side wall thereof, the second plurality of holes including a first sheath hole and a second sheath hole;

wherein the conduit and the multiport valve assembly are configured to exhibit at least a first selected orientation and a second selected orientation, and wherein:

in the first selected orientation, the conduit and the multiport valve assembly are configured to have the first conduit hole and the first sheath hole aligned and the second conduit hole and the second sheath hole not aligned; and in the second selected orientation, the conduit and the multiport valve assembly are configured to have the first conduit hole and the first sheath hole not aligned and the second conduit hole and the second sheath hole aligned.

2. The fluid collection device of claim 1 wherein:

the conduit includes a terminal end, the terminal end of the conduit defining the first plurality of holes thereon, and the multiport valve assembly includes a sheath concentrically disposed over the terminal end of the conduit within the interior chamber, the sheath defining a second plurality of holes therein; and the first plurality of holes and the second plurality of holes are spaced to align only one of the first plurality of holes with only one of the second plurality of holes for a selected orientation of the terminal end with respect to the sheath.

3. The fluid collection device of claim 2, further comprising an alignment assembly disposed on a first end of the fluid impermeable barrier, the alignment assembly including:

a fixed collar operably coupled to the fluid impermeable barrier; and an inner collar disposed within the fixed collar, the inner collar at least one of:

coupled to and positioned between a first portion of the conduit at least partially disposed in the chamber and a second portion of the conduit at least partially disposed outside of the chamber; or integrally formed with and positioned between the first portion of the conduit at least partially disposed in the chamber and the second portion of the conduit at least partially disposed outside of the chamber.

4. The fluid collection device of claim 2, wherein the sheath is only disposed in the chamber.

5. The fluid collection device of claim 2 wherein:

the first plurality of holes only include the first conduit hole and the second conduit hole, wherein the first conduit holing is a conduit distal hole on a first side of the conduit at a second end region of the fluid collection device, and wherein the second conduit hole is a conduit medial hole on a second side of the conduit and longitudinally spaced from the conduit distal hole by a first distance;

the second plurality of holes only includes the first sheath hole and the second sheath hole, wherein the first sheath hold is a sheath distal hole on a first side of the sheath at a second end region of the fluid collection device, and wherein the second sheath hole is a sheath medial hole on the first side of sheath and longitudinally spaced from the sheath distal hole by the first distance.

6. The fluid collection device of claim 1 wherein:

the first conduit hole is a conduit distal hole on a first side of the conduit at a second end region of the fluid collection device, and the second conduit hole is a conduit medial hole on a second side of the conduit and longitudinally spaced from the conduit distal hole by a first distance;

the first sheath hole is a sheath distal hole on a first side of the sheath at a second end region of the fluid collection device, and the second sheath hole a sheath medial hole on the first side of sheath and longitudinally spaced from the sheath distal hole by the first distance; and the conduit is rotatable with respect to the sheath.

7. The fluid collection device of claim 6, further comprising an alignment assembly disposed around the conduit on a first end of the fluid impermeable barrier, the alignment assembly including:

a fixed collar operably coupled to the fluid impermeable barrier; and an inner collar operably coupled to the terminal end of the conduit, the inner collar being disposed within the fixed collar;

wherein the fixed collar and the inner collar have markings to align the conduit distal hole with the sheath distal hole in the first selected orientation and the conduit medial hole with the sheath medial hole in the second selected orientation.

8. The fluid collection device of claim 7 wherein:

the markings on the fixed collar correspond to a position of the sheath distal hole and the sheath medial hole on the sheath; and the markings on the inner collar correspond to a position of the conduit distal hole and the conduit medial hole on the conduit.

9. The fluid collection device of claim 1 wherein the fluid permeable body includes a fluid permeable support and a fluid permeable membrane disposed over at least a portion of the fluid permeable support.

10. The fluid collection device of claim 1, further comprising at least one reservoir within the interior chamber.

11. The fluid collection device of claim 10 wherein the at least one reservoir includes one or more of a first reservoir located at a second end region of the fluid collection device or a second reservoir located in a medial portion of the fluid collection device.

12. The fluid collection device of claim 11, wherein the first reservoir and the second reservoir are substantially unoccupied.

13. The fluid collection device of claim 12, wherein the second reservoir is located in a medial portion of the fluid collection device, the second reservoir extending from the second sheath hole to the fluid impermeable barrier.

14. The fluid collection device of claim 1, wherein the multiport valve assembly is configured to selectively remove at least one of air or bodily fluids from different regions of the chamber via the conduit.

15. A fluid collection system, the system comprising:

a fluid collection device including, a fluid impermeable barrier at least partially defining an interior chamber and an opening through which the interior chamber is exposed to an external environment, a fluid permeable body positioned at least partially within the interior chamber to extend across at least a portion of the opening and configured to wick fluid away from the opening, a conduit extending into the interior chamber, the conduit defining a first plurality of holes on a side wall thereof, the first plurality of holes including a first conduit hole and a second conduit hole, and a multiport valve assembly disposed within the interior chamber, the multiport valve assembly including a sheath concentrically disposed over at least a portion of the conduit within the interior chamber, the sheath defining a second plurality of holes on a side wall thereof, the second plurality of holes including a first sheath hole and a second sheath hole;

wherein the conduit and the multiport valve assembly are configured to exhibit at least a first selected orientation and a second selected orientation, and wherein:

in the first selected orientation, the conduit and the multiport valve assembly are configured to have the first conduit hole and the first sheath hole aligned and the second conduit hole and the second sheath hole not aligned; and in the second selected orientation, the conduit and the multiport valve assembly are configured to have the first conduit hole and the first sheath hole not aligned and the second conduit hole and the second sheath hole aligned;

a fluid storage container fluidly connected to the fluid collection device via the conduit, the fluid storage container being configured to store fluids therein; and a vacuum source fluidly connected to the fluid storage container, the vacuum source being configured to provide vacuum force into the interior chamber via the fluid storage container and the conduit.

16. The fluid collection system of claim 15 wherein the fluid storage container includes a canister.

17. The fluid collection system of claim 16 wherein the vacuum source includes one or more of a vacuum pump, a wall-mounted vacuum line, or a hand pump.

18. A method to collect bodily fluid, the method comprising:

positioning a fluid collection device adjacent to a urethra of a wearer, the fluid collection device including:

a fluid impermeable barrier at least partially defining an interior chamber and an opening through which the interior chamber is exposed to an external environment, a fluid permeable body positioned at least partially within the interior chamber to extend across at least a portion of the opening and configured to wick fluid away from the opening, a conduit extending into the interior chamber, the conduit defining a first plurality of holes on a side wall thereof, the first plurality of holes including a first conduit hole and a second conduit hole, and a multiport valve assembly disposed within the interior chamber, the multiport valve assembly including a sheath concentrically disposed over at least a portion of the conduit within the interior chamber, the sheath defining a second plurality of holes on a side wall thereof, the second plurality of holes including a first sheath hole and a second sheath hole;

wherein the conduit and the multiport valve assembly are configured to exhibit at least a first selected orientation and a second selected orientation, and wherein:

in the first selected orientation, the conduit and the multiport valve assembly are configured to have the first conduit hole and the first sheath hole aligned and the second conduit hole and the second sheath hole not aligned; and in the second selected orientation, the conduit and the multiport valve assembly are configured to have the first conduit hole and the first sheath hole not aligned and the second conduit hole and the second sheath hole aligned;

receiving fluid from the urethra into the fluid collection device; and removing the fluid from the fluid collection device via the multiport valve assembly and the conduit.

19. The method of claim 18, further comprising selecting a port of the multiport valve assembly by switching to the first selected orientation or the second selected orientation.

20. The method of claim 19 wherein selecting a port includes rotating the conduit with respect to the sheath.

21. The method of claim 18 wherein receiving fluid from the urethra into the fluid collection device includes wicking the fluid into the fluid permeable body.

22. The method of claim 18 wherein removing the fluid from the fluid collection device via the conduit includes applying a vacuum in the interior chamber via a port of the multiport valve assembly.

* * * * *